United States Patent
Harper et al.

(10) Patent No.: US 6,933,313 B2
(45) Date of Patent: Aug. 23, 2005

(54) SUBSTITUTED CARBAZOLES AS INHIBITORS OF SPLA$_2$

(75) Inventors: Richard Waltz Harper, Indianapolis, IN (US); Ho-Shen Lin, Indianapolis, IN (US); Michael Enrico Richett, Indianapolis, IN (US)

(73) Assignee: Eli Lilly and Company, Indianapolis, IN (US)

(*) Notice: Subject to any disclaimer, the term of this patent is extended or adjusted under 35 U.S.C. 154(b) by 171 days.

(21) Appl. No.: 10/467,965

(22) PCT Filed: Mar. 15, 2002

(86) PCT No.: PCT/US02/06636

§ 371 (c)(1),
(2), (4) Date: Aug. 14, 2003

(87) PCT Pub. No.: WO02/079154

PCT Pub. Date: Oct. 10, 2002

(65) Prior Publication Data

US 2004/0087796 A1 May 6, 2004

Related U.S. Application Data

(60) Provisional application No. 60/279,300, filed on Mar. 28, 2001.

(51) Int. Cl.$^7$ ................... A61K 31/403; C07D 209/88
(52) U.S. Cl. ........................ 514/411; 548/441
(58) Field of Search ................. 514/411; 548/441

(56) References Cited

U.S. PATENT DOCUMENTS 5,420,289 A   5/1995   Musser et al.

FOREIGN PATENT DOCUMENTS

| EP | 0 950 657 | 10/1999 |
|----|-----------|---------|
| EP | 0 950 661 | 10/1999 |
| WO | WO 91/06537 | 5/1991 |
| WO | WO 01/21587 | 3/2001 |
| WO | WO 01/49662 | 7/2001 |

OTHER PUBLICATIONS

Dillard, et al., "Indole inhibitors of human nonpancreatic secretory phospholipase A21. Indole–3–acetamides," Journal of Medicinal Chemistry, American Chemical Society, vol. 39, No. 26, pp. 5119–5136; XP002046054, Dec. 1, 1996.

Bernard, et al., "A molecular modeling and 3D QSAR study of a large series of indole inhibitors of human non–pancreatic secretory phospholipase A2," European Journal of Medicinal Chemistry, Editions Scientifique Elsevier, vol. 36, No. 1, pp. 1–19; XP004317457, 2001.

*Primary Examiner*—Taofiq Solola
(74) *Attorney, Agent, or Firm*—Francis O. Ginah

(57) ABSTRACT

Carbazoles of formula (I) with R$^2$=hydroxyfunctional amide (hydroxamic or esters) are disclosed together with the use of such compounds for inhibiting sPLA$_2$ mediated release of fatty acids for treatment of conditions such as septic shock.

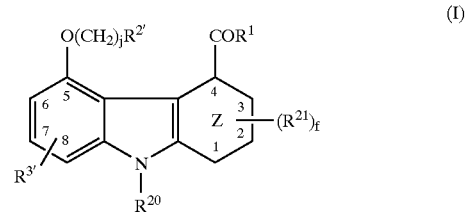

12 Claims, No Drawings

SUBSTITUTED CARBAZOLES AS INHIBITORS OF SPLA₂

This application claims the benefit of Provisional Application No. 60/279,300, filed Mar. 28, 2001.

FIELD OF THE INVENTION

This invention relates to novel substituted carbazole compounds useful for inhibiting sPLA$_2$ mediated release of fatty acids for conditions such as septic shock.

BACKGROUND INFORMATION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of April 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of April 5, pp. 5768–5775, 1989; the disclosures of which are incorporated herein by reference.

Alexander, et al., U.S. Pat. Nos. 3,939,177 and 3,979,391, disclose 1,2,3,4-tetrahydrocarbazoles useful as antibacterial agents.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$ such as septic shock, adult respiratory distress syndrome, pancreatitis, trauma-induced shock, bronchial asthma, allergic rhinitis, rheumatoid arthritis, etc.

It is desirable to develop new compounds and treatments for sPLA$_2$ induced diseases.

SUMMARY OF THE INVENTION

This invention provides substituted carbazole compounds as depicted in the general formula (I) below:

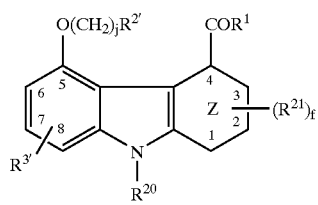

(I)

wherein;

Z is cyclohexenyl, or phenyl, $R^{20}$ is selected from groups (a), (b) and (c) where;

(a) is —(C$_1$–C$_{20}$)alkyl, —(C$_2$–C$_{20}$)alkenyl, —(C$_2$–C$_{20}$)alkynyl, carbocyclic radicals, or heterocyclic radicals, or (b) is a member of (a) substituted with one or more independently selected non-interfering substituents; or (c) is the group —(L)—$R^{80}$; where, (L)—is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) a carbon, hydrogen, and oxygen only; and where $R^{80}$ is a group selected from (a) or (b);

$R^{21}$ is a non-interfering substituent where f is 1–3;

$R^1$ is —NHNR$^{30}$R$^{31}$, —NR$^{30}$R$^{31}$, or —CONR$^{30}$R$^{31}$, where R$^{30}$ and R$^{31}$ are each independently hydrogen or —(C$_1$–C$_6$)alkyl;

$R^{2'}$ is —CONR$^{40}$R$^{41}$, where R$^{40}$ —OH, —O(C$_1$–C$_8$)alkyl, —O(C$_2$–C$_8$)alkenyl, —O(C$_3$–C$_8$)cycloalkyl, —O(aryl) and —O(C$_1$–C$_8$)alkylaryl; and R$^{41}$ is hydrogen, —(C$_1$–C$_8$)alkyl, —(C$_2$–C$_8$)alkenyl, —(C$_3$–C$_8$) cycloalkyl, aryl and —(C$_1$–C$_8$)alkylaryl;

$R^{3'}$ is selected from non-interfering substituents, carbocyclic radicals, carbocyclic radicals substituted with non-interfering substituents, heterocyclic radicals, and heterocyclic radicals substituted with non-interfering substituents; and j is 1 to 3 both inclusive;

or a pharmaceutically acceptable solvate or salt, thereof.

These substituted carbazoles are effective in inhibiting human sPLA$_2$ mediated release of fatty acids.

This invention is also a pharmaceutical formulation comprising a compound of formula I in association with one or more pharmaceutically acceptable diluents, carriers and excipients.

This invention is also a method of inhibiting sPLA$_2$ comprising administering to a mammal in need of such treatment a therapeutically effective amount of a compound of formula I.

According to a further aspect of the present invention, there is provided a method of selectively inhibiting sPLA$_2$ in a mammal in need of such treatment comprising administering to said mammal a therapeutically effective amount of a compound of formula I.

This invention, further provides a compound of formula I for use as a medicament in the treatment of inflammatory diseases such as sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis and related diseases which comprises administering to a mammal in need of such treatment a therapeutically effective amount of the compound of formula I in an amount sufficient to inhibit sPLA$_2$ mediated release of fatty acid and to thereby inhibit or prevent the arachidonic acid cascade and its deleterious products.

This invention provides, in addition, a process for preparing compounds of formula I below:

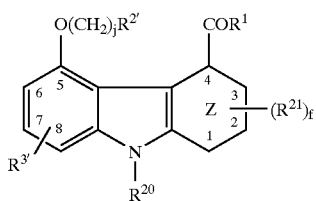

(I)

wherein;

Z is cyclohexenyl, or phenyl, $R^{20}$ is selected from groups (a), (b) and (c) where;

(a) is —($C_1$–$C_{20}$)alkyl, —($C_2$–$C_{20}$)alkenyl, —($C_2$–$C_{20}$) alkynyl, carbocyclic radicals, or heterocyclic radicals, or (b) is a member of (a) substituted with one or more independently selected non-interfering substituents; or (c) is the group —(L)—$R^{80}$; where, (L)— is a divalent linking group of 1 to 12 atoms selected from carbon, hydrogen, oxygen, nitrogen, and sulfur; wherein the combination of atoms in —(L)— are selected from the group consisting of (i) carbon and hydrogen only, (ii) one sulfur only, (iii) one oxygen only, (iv) one or two nitrogen and hydrogen only, (v) carbon, hydrogen, and one sulfur only, and (vi) a carbon, hydrogen, and oxygen only; and where $R^{80}$ is a group selected from (a) or (b);

$R^{21}$ is a non-interfering substituent where f is 1–3;

$R^1$ is —NHNR$^{30}$R$^{31}$, —NR$^{30}$R$^{31}$, or —CONR$^{30}$R$^{31}$, where $R^{30}$ and $R^{31}$ are each independently hydrogen or —($C_1$–$C_6$)alkyl;

$R^{2'}$ is —CONR$^{40}$R$^{41}$, where $R^{40}$ —OH, —O($C_1$–$C_8$)alkyl, —O($C_2$–$C_8$)alkenyl, —O($C_3$–$C_8$)cycloalkyl, —O(aryl) and —O($C_1$–$C_8$)alkylaryl; and $R^{41}$ is hydrogen, —($C_1$–$C_8$)alkyl, —($C_2$–$C_8$)alkenyl, —($C_3$–$C_8$) cycloalkyl, aryl and —($C_1$–$C_8$)alkylaryl;

$R^{3'}$ is selected from non-interfering substituents, carbocyclic radicals, carbocyclic radicals substituted with non-interfering substituents, heterocyclic radicals, and heterocyclic radicals substituted with non-interfering substituents; and j is 1 to 3 both inclusive;

or a pharmaceutically acceptable solvate or salt, thereof;

comprising reacting a compound of the formula II:

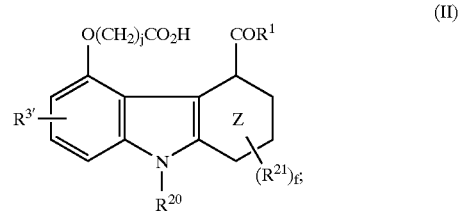

(II)

where $R^1$, $R^{3'}$, $R^{20}$, $R^{21}$, Z, f and j are as defined above; with an amine of the formula HN($R^{40}R^{41}$) where $R^{40}$ is —OH, —O($C_1$–$C_8$)alkyl, —O($C_2$–$C_9$)alkenyl, —O($C_3$–$C_8$)cycloalkyl, —O(aryl) and —O($C_1$–$C_8$) alkylaryl; and $R^{41}$ is hydrogen, —($C_1$–$C_8$)alkyl, —($C_2$–$C_8$)alkenyl, —($C_3$–$C_8$)cycloalkyl, aryl and —($C_1$–$C_8$)alkylaryl.

Other objects, features and advantages of the present invention will become apparent from the subsequent description and the appended claims.

DETAILED DESCRIPTION OF THE INVENTION

Definitions

As used herein, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl tert butyl, n-pentyl, isopentyl, neopentyl, heptyl, hexyl, octyl, nonyl, decyl, undecyl, dodecyl, tridecyl, tetradecyl and the like. The term "alkyl" includes —($C_1$–$C_2$)alkyl, —($C_1$–$C_4$)alkyl, —($C_1$–$C_6$)alkyl, —($C_5$–$C_{14}$)alkyl, and —($C_1$–$C_{10}$)alkyl.

The term "aryl" means an aromatic carbocyclic structure having six to ten carbon atoms. Examples of such ring structures are phenyl, naphthyl and the like. The aryl group can be unsubstituted or can have one or two non-interfering substituents at any available position the aryl ring.

Preferred substituents on the aryl group include —($C_1$–$C_{14}$)alkyl, —($C_2$–$C_6$)alkenyl, —($C_2$–$C_6$)alkynyl, —($C_7$–$C_{12}$)aralkyl, —($C_7$–$C_{12}$)alkaryl, —($C_3$–$C_8$) cycloalkyl, —($C_3$–$C_8$)cycloalkenyl, phenyl, tolulyl, —($C_1$–$C_6$)alkoxy, —($C_2$–$C_6$)alkenyloxy, —($C_2$–$C_6$) alkynyloxy, —($C_1$–$C_{12}$)alkoxyalkyl, —($C_1$–$C_{12}$) alkoxyalkyloxy, —($C_1$–$C_{12}$)alkylcarbonyl, —($C_1$–$C_{12}$) alkylcarbonylamino, —($C_1$–$C_{12}$)alkoxyamino, —($C_1$–$C_{12}$) alkoxyaminocarbonyl, —($C_1$–$C_{12}$)alkylamino, —($C_1$–$C_6$) alkylthio, —($C_1$–$C_{12}$)alkylthiocarbonyl, —($C_1$–$C_6$) alkylsulfonyl, —($C_1$–$C_6$)haloalkylsulfonyl, —($C_1$–$C_6$) haloalkylsulfonyl, —($C_1$–$C_6$)hydroxyalkyl, —($CH_2$)$_n$CN, —($CH_2$)$_n$NR$^9$R$^{10}$, —(C(O)O($C_1$–$C_6$)alkyl, —($CH_2$)$_n$O ($C_1$–$C_6$)alkyl, benzyloxy, phenoxy, phenylthio, —(CONHSO$_2$)R$^{15}$, —CHO, —CF$_3$, —OCF$_3$, pyridyl, amino, amidino, halo, carbonyl, carboxyl, carbolkoxy, —($CH_2$)$_n$CO$_2$H, cyano, cyanoquanidinyl, quanidino, hydroxy, hydroxyamino, nitro, —SO$_3$H, furyl, thiophenyl, —COR$^9$, —CONR$^9$R$^{10}$, —NR$^9$R$^{10}$, —NCHCOR$^9$, —SO$_2$R$^9$, —OR$^9$, SR$^9$, —CH$_2$SO$_2$R$^9$, tetrazoyl, tetrazolyl substituted with —($C_1$–$C_6$)alkyl, phenyl or —($C_1$–$C_4$) alkylphenyl;, —($CH_2$)$_n$OSi($C_1$–$C_6$)$_3$alkyl or ($C_1$–$C_6$) alkylcarbonyl; where $R^9$ and $R^{10}$ are independently hydrogen, —CF$_3$, phenyl, —($C_1$–$C_4$)alkyl or —($C_1$–$C_4$) alkylphenyl, where $R^{15}$ is —($C_1$–$C_6$)alkyl, —CF$_3$, naphthyl or (CH$_2$)s phenyl, where n is from 1 to 8 and where s is 0 to 5.

Preferred "aryl" substituents include —(C$_1$–C$_{14}$)alkyl, —(C$_3$–C$_8$)cycloalky, phenyl, —(C$_1$–C$_6$)alkylsulfonyl, and —SO$_2$R$^9$ where R$^9$ is hydrogen, —CF$_3$, phenyl, —(C$_1$–C$_4$)alkyl or —(C$_1$–C$_4$)alkylphenyl.

The term "alkenyl" as used herein represents an olefinically unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2-heptenyl, 3-heptenyl, 4-heptenyl, 5-heptenyl, 6-heptenyl as well as dienes and trienes of straight and branched chains.

The term "alkynyl" denotes such radicals as ethynyl, propynyl, butynyl, pentynyl, hexynyl, heptynyl as well as di- and tri-ynes.

The term "halo" means chloro, fluoro, bromo or iodo.

The term "—(C$_1$–C$_4$)alkoxyl", as used herein, denotes a group such as methoxy, ethoxy, n-propoxy, isopropoxy, n-butoxy, t-butoxy and like groups, attached to the remainder of the molecule by the oxygen atom.

The term "phenyl(C$_1$–C$_4$)alkyl" refers to a straight or branched chain alkyl group having from one to four carbon atoms attached to a phenyl ring which chain is attached to the remainder of the molecule. Typical phenylalkyl groups include benzyl, phenylethyl, phenylpropyl, phenylisopropyl, and phenylbutyl.

The term "—(C$_1$–C$_4$)alkylthio" defines a straight or branched alkyl chain having one to four carbon atoms attached to the remainder of the molecule by a sulfur atom. Typical —(C$_1$–C$_4$)alkylthio groups include methylthio, ethylthio, propylthio, butylthio and the like.

The term "—(C$_3$–C$_{14}$)cycloalkyl" includes groups such as cyclopropyl, cyclobutyl, cyclopentyl, cyclohexyl, cycloheptyl, cyclooctyl, cyclononyl, cyclodecyl, cycloundecyl, cyclododecyl, cyclotridecyl, cyclotetradecyl and the like. The term "—(C$_3$–C$_{14}$)cycloalkyl", includes —(C$_3$–C$_7$)cycloalkyl.

The term, "heterocyclic radical", refers to radicals derived from monocyclic or polycyclic, saturated or unsaturated, substituted or unsubstituted heterocyclic nuclei having 5 to 14 ring atoms and containing from 1 to 3 hetero atoms selected from the group consisting of nitrogen, oxygen or sulfur. Typical heterocyclic radicals are pyridyl, thienyl, fluorenyl, pyrrolyl, furanyl, thiophenyl, pyrazolyl, imidazolyl, phenylimidazolyl, triazolyl, tetrazole, isoxazolyl, oxazolyl, thiazolyl, thiadiazolyl, indolyl, carbazolyl, norharmanyl, azaindolyl, benzofuranyl, dibenzofuranyl, thianaphtheneyl, dibenzothiophenyl, indazolyl, imidazo(1.2-A)pyridinyl, benzotriazolyl, anthranilyl, 1,2-benzisoxazolyl, benzoxazolyl, benzothiazolyl, purinyl, pryidinyl, dipyridylyl, phenylpyridinyl, benzylpyridinyl, pyrimidinyl, phenylpyrimidinyl, pyrazinyl, 1,3,5-triazinyl, quinolinyl, phthalazinyl, quinazolinyl, and quinoxalinyl.

The term "carbocyclic radical" refers to radicals derived from a saturated or unsaturated, substituted or unsubstituted 5 to 14 membered organic nucleus whose ring forming atoms (other than hydrogen) are solely carbon atoms. Typical carbocyclic radicals are cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexeyl, acenaphthylenyl, and anthracenyl, biphenyl, bibenzylyl and related bibenzylyl homologues represented by the formula (bb),

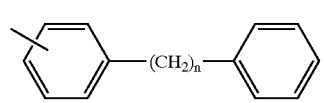

(bb)

where n is an integer from 1 to 8.

The term, "non-interfering substituent", refers to radicals suitable for substitution at positions 1, 2, 3, 6, 7 and/or 8 on the tricyclic nucleus and radical(s) suitable for substitution on the heterocyclic radical and carbocyclic radical as defined above. Illustrative non-interfering radicals are hydrogen, —(C$_1$–C$_{14}$)alkyl, —(C$_2$–C$_6$)alkenyl, —(C$_2$–C$_6$)alkynyl, —(C$_7$–C$_{12}$)aralkyl, —(C$_7$–C$_{12}$)alkaryl, —(C$_3$–C$_8$)cycloalkyl, —(C$_3$–C$_8$)cycloalkenyl, phenyl, tolulyl, xylenyl, biphenyl, —(C$_1$–C$_6$)alkoxy, —(C$_2$–C$_6$)alkenyloxy, —(C$_2$–C$_6$)alkynyloxy, —(C$_1$–C$_{12}$)alkoxyalkyl, —(C$_1$–C$_{12}$)alkoxyalkyloxy, —(C$_1$–C$_{12}$)alkylcarbonyl, —(C$_1$–C$_{12}$)alkylcarbonylamino, —(C$_1$–C$_{12}$)alkoxyamino, —(C$_1$–C$_{12}$)alkoxyaminocarbonyl, —(C$_1$–C$_{12}$)alkylamino, —(C$_1$–C$_6$)alkylthio, —(C$_1$–C$_{12}$)alkylthiocarbonyl, —(C$_1$–C$_6$)alkylsulfinyl, —(C$_1$–C$_6$)alkylsulfonyl, —(C$_1$–C$_6$)haloalkoxy, —(C$_1$–C$_6$)haloalkylsulfonyl, —(C$_1$–C$_6$)haloalkyl, —(C$_1$–C$_6$)hydroxyalkyl, —(CH$_2$)$_n$CN, —(CH$_2$)$_n$NR$^9$R$^{10}$, —C(O)O(C$_1$–C$_6$alkyl), —(CH$_2$)$_n$O(C$_1$–C$_6$ alkyl), benzyloxy, phenoxy, phenylthio; —(CONHSO$_2$)R$^{15}$, —CHO, —CF$_3$, —OCF$_3$, pyridyl, amino, amidino, halo, carbamyl, carboxyl, carbalkoxy, —(CH$_2$)$_n$CO$_2$H, cyano, cyanoguanidinyl, guanidino, hydrazide, hydrazino, hydrazido, hydroxy, hydroxyamino, nitro, phosphono, —SO$_3$H, thioacetal, thiocarbonyl, furyl, thiophenyl —COR$^9$, —CONR$^9$R$^{10}$, —NR$^9$R$^{10}$, —NCHCOR$^9$, —SO$_2$R$^9$, —OR$^9$, —SR$^9$, CH$_2$SO$_2$R$^9$, tetrazolyl, tetrazolyl substituted with —(C$_1$–C$_6$)alkyl, phenyl or —(C$_1$–C$_4$)alkylphenyl; —(CH$_2$)$_n$OSi(C$_1$–C$_6$)$_3$alkyl and (C$_1$–C$_6$)alkylcarbonyl; where R$^9$ and R$^{10}$ are independently hydrogen, —CF$_3$, phenyl, —(C$_1$–C$_4$)alkyl or —(C$_1$–C$_4$)alkylphenyl, where R is —(C$_1$–C$_6$)alkyl, —CF$_3$, naphthyl or —(CH$_2$)$_s$phenyl, where n is from 1 to 8 and where s is from 0 to 5.

A preferred group of non-interfering substituents include hydrogen, —(C$_1$–C$_6$)alkyl, —(C$_2$–C$_6$)alkenyl, —(C$_2$–C$_6$)alkynyl, —(C$_3$–C$_8$)cycloalkyl, —(C$_1$–C$_6$)alkoxy, halo or -phenyl(C$_1$–C$_4$)alkyl.

Another preferred group of non-interfering substituents include hydrogen, halo, —(C$_1$–C$_3$)alkyl, —(C$_3$–C$_4$)cycloalkyl, —(C$_5$–C$_8$)cycloalkenyl, —O(C$_1$–C$_2$)alkyl and —S(C$_1$–C$_2$)alkyl.

The salts of the above tricyclics are an additional aspect of the invention. In those instances where the compounds of the invention possess acidic functional groups various salts may be formed which are more water soluble and physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1–19 (1977)).

Compounds of the invention may have chiral centers and exist in optically active forms. R— and S— isomers and racemic mixtures are contemplated by this invention. A particular stereoisomer may be prepared by known methods using stereospecific reactions with starting materials containing asymmetric centers already resolved or, alternatively, by subsequent resolution of mixtures of stereoisomers using known methods.

The term "acid protecting group" is used herein as it is frequently used in synthetic organic chemistry, to refer to a group which will prevent an acid group from participating in a reaction carried out on some other functional group in the molecule, but which can be removed when it is desired to do so. Such groups are discussed by T. W. Greene in chapter 5 of "Protective Groups" in *Organic Synthesis*, John Wiley and Sons, New York, 1981, incorporated herein by reference in its entirety.

Examples of acid protecting groups include ester or amide derivatives of the acid group, such as, methyl, methoxymethyl, methyl-thiomethyl, tetrahydropyranyl, methoxyethoxymethyl, benzyloxymethyl, phenyl, aryl, ethyl, 2,2,2-trichloroethyl, 2-methylthioethyl, t-butyl, cyclopentyl, triphenylmethyl, diphenylmethyl, benzyl, trimethylsilyl, N,N-dimethyl, pyrrolidinyl, piperidinyl, or o-nitroanilide. A preferred acid-protecting group is methyl.

PREFERRED COMPOUNDS OF THE INVENTION

Preferred Subgroups of Compounds

A preferred subclass of compounds are those wherein $R^{21}$ is selected from the group hydrogen, halo, —($C_1$–$C_3$)alkyl, —($C_3$–$C_4$)cycloalkyl, —($C_5$–$C_8$)cycloalkenyl, —O($C_1$–$C_2$)alkyl and —S($C_1$–$C_2$)alkyl.

Another preferred subclass of compounds are those wherein for $R^{20}$, group $R^{80}$ is selected from the group consisting of cycloalkyl, cycloalkenyl, phenyl, naphthyl, norbornanyl, bicycloheptadienyl, tolulyl, xylenyl, indenyl, stilbenyl, terphenylyl, diphenylethylenyl, phenylcyclohexenyl, acenaphthylenyl, and anthracenyl, biphenyl, bibenzylyl and related bibenzylyl homologues represented by the formula (bb),

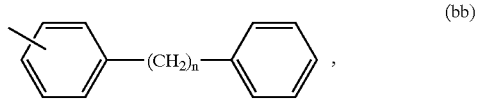

(bb)

where n is a number from 1 to 8. Particularly preferred are compounds wherein $R^{20}$ is selected from the group consisting of

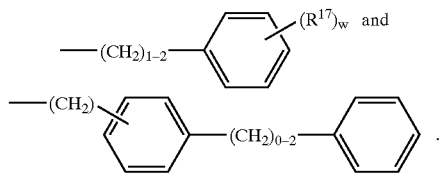

where $R^{17}$ is independently selected from hydrogen, halo, —($C_1$–$C_{10}$)alkyl, —($C_1$–$C_{10}$)alkoxy, —S—($C_1$–$C_{10}$ alkyl), and —($C_1$–$C_{10}$)haloalkyl, and w is a number from 1 to 5.

Another preferred subclass of compounds are those wherein the non-interfering substituents are selected from the group consisting of hydrogen, —($C_1$–$C_6$)alkyl, —($C_2$–$C_6$)alkenyl, —($C_2$–$C_6$)alkynyl, —($C_7$–$C_{12}$)aralkyl, —($C_7$–$C_{12}$)alkaryl, —($C_3$–$C_8$)cycloalkyl, —($C_3$–$C_8$) cycloalkenyl, phenyl, tolulyl, xylenyl, biphenyl, —($C_1$–$C_6$) alkoxy, —($C_2$–$C_6$)alkenyloxy —($C_2$–$C_6$)alkynyloxy, —($C_1$–$C_{12}$)alkoxyalkyl, —($C_1$–$C_{12}$)alkoxyalkyloxy, —($C_1$–$C_{12}$)alkylcarbonyl, —($C_1$–$C_{12}$)alkylcarbonylamino, —($C_1$–$C_{12}$)alkoxyamino, —($C_1$–$C_{12}$)alkoxyaminocarbonyl, —($C_1$–$C_{12}$)alkylamino, —($C_1$–$C_6$)alkylthio, —($C_1$–$C_{12}$) alkylthiocarbonyl, —($C_1$–$C_6$)alkylsulfinyl, —($C_1$–$C_6$) alkylsulfonyl, —($C_1$–$C_6$)haloalkoxy, —($C_1$–$C_6$) haloalkylsulfonyl, —($C_1$–$C_6$)haloalkyl, —($C_1$–$C_6$) hydroxyalkyl, —C(O)O($C_1$–$C_6$ alkyl), —($CH_2$)$_n$O($C_1$–$C_6$ alkyl), benzyloxy, halo, phenylthio; phenyl substituted with —($C_1$–$C_6$)alkyl, halo, or —$CF_3$; furyl, thiophenyl, —($CH_2$)$_n$ CN, —($CH_2$)$_n$$R^8$, —CHO, amino, amidino, carbamyl, carboxyl, carbalkoxy, —($CH_2$)$_n$$CO_2$H, cyano, cyanoguanidinyl, guanidino, hydrazide, hydrazino, hydrazido, hydroxy, hydroxyamino, nitro, phosphono, —$SO_3$H, thioacetal, thiocarbonyl, and —($C_1$–$C_6$) alkylcarbonyl; where $R^8$ is hydrogen, —$CONH_2$, —$NR^9R^{10}$, —CN or phenyl, where $R^9$ and $R^{10}$ are independently —($C_1$–$C_4$)alkyl or -phenyl($C_1$–$C_4$) and where n is from 1 to 8.

Another preferred group of non-interfering substituents include hydrogen, —O($C_1$–$C_4$)alkyl, halo, —($C_1$–$C_6$)alkyl, phenyl, —($C_1$–$C_4$)alkylphenyl; phenyl substituted with —($C_1$–$C_6$)alkyl, halo, or —$CF_3$; —$CH_2$OSi($C_1$–$C_6$)$_3$alkyl, furyl, thiophenyl, —($C_1$–$C_6$)hydroxyalkyl; or —($CH_2$)$_n$$R^8$ where $R^8$ is hydrogen, —$CONH_2$, —$NR^9R^{10}$, —CN or phenyl, where $R^9$ and $R^{10}$ are independently —($C_1$–$C_4$)alkyl or -phenyl($C_1$–$C_4$)alkyl and where n is 1 to 8.

Even more preferred non-interfering substituents are hydrogen, —($C_1$–$C_6$)alkyl, —($C_2$–$C_6$)alkenyl, —($C_2$–$C_6$) alkynyl, —($C_3$–$C_8$)cycloalkyl, —($C_1$–$C_6$)alkoxy, halo or —($C_1$–$C_4$)alkyl phenyl.

Preferred compounds of the invention are those having the general formula (III):

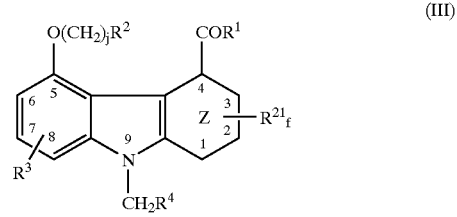

(III)

wherein;

Z is cyclohexenyl, or phenyl, $R^1$ is —$NHNR^{30}R^{31}$, —$NR^{30}R^{31}$, or —$CONR^{30}R^{31}$, where $R^{30}$ and $R^{31}$ are each independently hydrogen or —($C_1$–$C_6$)alkyl;)

$R^2$ is —$CONR^{40}R^{41}$, where $R^{40}$ is —OH, —O($C_1$–$C_8$)alkyl, —O($C_2$–$C_8$)alkenyl, —O($C_3$–$C_8$)cycloalkyl, —O(aryl) or —O($C_1$–$C_8$)alkylaryl; and $R^{41}$ is hydrogen, —($C_1$–$C_8$) alkyl, —($C_2$–$C_8$)alkenyl, —($C_3$–$C_8$)cycloalkyl, aryl or —($C_1$–$C_8$)alkylaryl;

$R^3$ is hydrogen, —O($C_1$–$C_6$)alkyl, halo, —($C_1$–$C_6$)alkyl, —($C_2$–$C_6$)alkenyl, —($C_2$–$C_6$)alkynyl, —($C_3$–$C_8$) cycloalkyl, phenyl, —($C_1$–$C_4$)alkylphenyl; phenyl substituted with —($C_1$–$C_6$)alkyl, halo, or —$CF_3$; —$CH_2$OSi ($C_1$–$C_6$)$_3$alkyl, furyl, thiophenyl, —($C_1$–$C_6$) hydroxyalkyl, —($C_1$–$C_6$)alkoxy($C_1$–$C_6$)alkyl, —($C_1$–$C_6$) alkoxy($C_1$–$C_6$)alkenyl, and —($CH_2$)$_n$$R^8$, where $R^8$ is hydrogen, —$CONH_2$, —$NR^9R^{10}$, —CN or phenyl, where $R^9$ and $R^{10}$ are independently hydrogen, —$CF_3$, phenyl, —($C_3$–$C_4$)alkyl, —($C_1$–$C_4$)alkylphenyl or -phenyl ($C_1$–$C_4$)alkyl and n is 1 to 8; and R$^4$ is hydrogen, —(C$_1$–C$_{14}$)alkyl, —(C$_3$–C$_{14}$)cycloalkyl, pyridyl, phenyl or phenyl substituted with from 1–5 substituents selected from the group consisting of —(C$_1$–C$_6$)alkyl, halo, —CF$_3$, —OCF$_3$, —(C$_1$–C$_4$)alkoxy, —CN, —(C$_1$–C$_4$)alkylthio, —(C$_1$–C$_4$)alkylphenyl, phenyl, phenoxy and —OR$^9$; where R$^9$ is independently hydrogen, —CF$_3$, phenyl, —(C$_1$–C$_4$)alkyl, —(C$_1$–C$_4$)alkylphenyl; tetrazole or tetrazole substituted with —(C$_1$–C$_4$)alkyl or —(C$_1$–C$_4$)alkylphenyl; or naphthyl;

R$^{21}$ is hydrogen, halo, —(C$_1$–C$_3$)alkyl, —(C$_3$–C$_4$) cycloalkyl, —(C$_3$–C$_8$)cycloalkenyl, —O(C$_1$–C$_2$)alkyl and —S(C$_1$–C$_2$)alkyl where f is 1 to 3; and j is 1 to 3 both inclusive;

or a pharmaceutically acceptable solvate or salt, thereof.

Preferred substituents of compounds of formula III include the following:

(a) R$^1$ is —NH$_2$, —NHNH$_2$;

(b) R$^1$ is —NH$_2$;

(c) R$^3$ is -hydrogen, —O(C$_1$–C$_4$)alkyl or —(CH$_2$)$_n$R$^8$, where n is 2 and R$^8$ is hydrogen or phenyl;

(d) R$^3$ is hydrogen, or —O(C$_1$–C$_4$ alkyl);

(e) R$^3$ $^{is}$, phenyl, —(C$_1$–C$_4$)alkylphenyl; phenyl substituted with —(C$_1$–C$_6$)alkyl, halo, or —CF$_3$;

(f) R$^3$ is —CH$_2$OSi(C$_1$–C$_6$)$_3$alkyl, furyl, thiophenyl;

(g) R$^3$ is —(C$_1$–C$_6$)hydroxyalkyl, —(C$_1$–C$_6$)alkoxy(C$_1$–C$_6$)alkyl, —(C$_1$–C$_6$)alkoxy(C$_1$–C$_6$)alkenyl;

(h) R$^4$ is hydrogen;

(i) R$^4$ is pyridyl;

(j) R$^4$ is phenyl or phenyl substituted with from 1–5 substituents selected from the group consisting of —(C$_1$–C$_6$)alkyl, halo, —CF$_3$, —OCF$_3$, —(C$_1$–C$_4$) alkoxy, —CN, —(C$_1$–C$_4$)alkylthio, —(C$_1$–C$_4$) alkylphenyl, phenyl, phenoxy and —OR$^9$; where R$^9$ is independently hydrogen, —CF$_3$, phenyl, —(C$_1$–C$_4$) alkyl, —(C$_1$–C$_4$)alkylphenyl;

(k) R$^4$ is tetrazole or tetrazole substituted with —(C$_1$–C$_4$) alkyl or —(C$_1$–C$_4$)alkylphenyl;

(l) R$^4$ is naphthyl;

(m) R$^2$ is —CONR$^{40}$R$^{41}$, where R$^{40}$ is —OH or —O(C$_1$–C$_8$)alkyl; and R$^{41}$ is hydrogen or —(C$_1$–C$_8$) alkyl;

(n) R$^2$ is —CONR$^{40}$R$^{41}$, where R$^{40}$ is —O(C$_2$–C$_8$) alkenyl or —O(C$_3$–C$_8$)cycloalkyl; and R$^{41}$ is hydrogen or —(C$_1$–C$_8$)alkyl;

(o) R$^2$ is —CONR$^{40}$R$^{41}$, where R$^{40}$ is —OH or —O(C$_1$–C$_8$)alkyl; and R$^{41}$ is —(C$_2$–C$_8$)alkenyl or —(C$_3$–C$_8$)cycloalkyl;

(p) R$^2$ is —CONR$^{40}$R$^{41}$, where R$^{40}$ is —OH or —O(C$_1$–C$_8$)alkyl; and R$^{41}$ is aryl or —(C$_1$–C$_8$) alkylaryl;

(q) R$^2$ is —CONR$^{40}$R$^{41}$, where R$^{40}$ is —OH, —O(C$_1$–C$_8$) alkyl, —O(C$_2$–C$_8$)alkenyl or —O(C$_3$–C$_8$)cycloalkyl; and R$^{41}$ is hydrogen, —(C$_1$–C$_8$)alkyl, —(C$_2$–C$_8$) alkenyl, —(C$_3$–C$_8$)cycloalkyl, aryl or —(C$_1$–C$_8$) alkylaryl;

(r) R$^2$ is —CONR$^{40}$R$^{41}$, where R$^{40}$ is —O(aryl) or —O(C$_1$–C$_8$)alkylaryl; and R$^{41}$ is hydrogen, —(C$_1$–C$_8$) alkyl, —(C$_2$–C$_8$)alkenyl, —(C$_3$–C$_8$)cycloalkyl, aryl and —(C$_1$–C$_8$)alkylaryl;

(s) R$^3$ is —(CH$_2$)$_n$R$^8$, where R$^8$ is —NR$^9$R$^{10}$,

or —CN, where R$^9$ and R$^{10}$ are independently hydrogen, or —(C$_1$–C$_4$)alkyl;

(t) R$^3$ is hydrogen, —(C$_1$–C$_6$)alkyl, —(C$_2$–C$_6$)alkenyl, —(C$_2$–C$_6$)alkynyl, —(C$_3$–C$_8$)cycloalkyl, —O(C$_1$–C$_6$) alkyl, halo or —(C$_1$–C$_4$)alkylphenyl;

(u) R$^3$ is phenyl substituted with —(C$_1$–C$_6$)alkyl, halo, or —CF$_3$;

(v) R$^3$ —CH$_2$OSi(C$_1$–C$_6$)$_3$alkyl, furyl, thiophenyl, —(C$_1$–C$_6$)hydroxyalkyl, —(C$_1$–C$_6$)alkoxy(C$_1$–C$_6$) alkyl, —(C$_1$–C$_6$)alkoxy(C$_1$–C$_6$)alkenyl;

(w) R$^4$ is phenyl;

(x) R$^4$ is phenyl substituted at the 2- and 6-position of the phenyl ring with —(C$_1$–C$_4$)alkyl, —(C$_1$–C$_4$)alkoxy, halo or phenyl;

(y) R$^4$ is phenyl substituted at the 2- or 6-position of the phenyl ring with —(C$_1$–C$_4$)alkyl, —(C$_1$–C$_4$)alkoxy, halo or phenyl;

(z) R$^4$ is phenyl substituted at the 3- or 5-position of the phenyl ring with —(C$_1$–C$_4$)alkyl, —(C$_1$–C$_4$)alkoxy, halo or phenyl;

(aa) R$^4$ is —(C$_1$–C$_{14}$)alkyl or —(C$_3$–C$_{14}$)cycloalkyl;

(bb) Z is cyclohexenyl;

(cc) Z is phenyl;

(dd) R$^1$ is CONR$^{30}$R$^{31}$ or CONH$_2$;

(ee) R$^1$ is NR$^{30}$R$^{31}$;

(ff) R$^1$ is NHNR$^{30}$R$^{31}$;

(gg) f is 1 or 2;

(hh) f is 3;

(ii) j is 1 or 2; and (jj) j is 3.

Some typical compounds of this invention are provided in tabular form: however, such named compounds are not intended to limit the scope of this invention in any way.

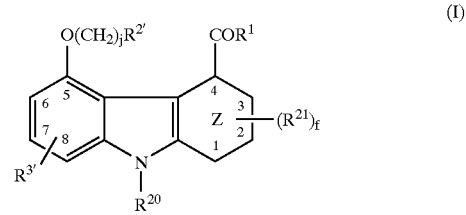

(I)

TABLE 1

| R$^1$ | R$^{2'}$ | R$^{20}$ | R$^{3'}$ | R$^{21}$ | Z | j |
|---|---|---|---|---|---|---|
| —NHNH$_2$ | —CONH(O-c-C$_3$H$_5$) | H | 6-CH$_2$Ph-o-OH$_2$CH$_3$ | H | Ph | 1 |
| —NH$_2$ | —CON(CH$_3$)(OH) | —(CH$_2$CH$_2$CH$_2$CH$_3$) | H | H | Ph | 1 |

TABLE 1-continued

| R¹ | R²' | R²⁰ | R³' | R²¹ | Z | j |
|---|---|---|---|---|---|---|
| —CONH₂ | —CON(CHCHCH₃)(OPh) | -(c-C₃—H₅) | 7-CH₂Osi(CH₃)₃ | H | Ph | 2 |
| —CONH(CH₂CH₃) | —CON(CH₂Ph) (OH) | Ph | H | 2-CH₂CH₃ | Ph | 1 |
| —NH₂ | —CON(-c-C₅H₉)(OCH₃) | Ph | H | H | Ph | 1 |
| —NH₂ | —CON(Ph-o-F)(OPh) | —Ph-o-CH₃ | 6-CH₂CH₃OH | H | Cx | 1 |
| —NH₂ | —CON(Ph)(OPh-o-Cl) | —Ph-m-Br | 7-CH₂OCH₃ | H | Ph | 1 |
| —NH₂ | —CONH(OC₃H₇) | —Ph-o-CH₃Ph—CF₃ | H | 1-OCH₂CH₃ | Cx | 3 |
| —N(CH₂CH₂CH₃)₂ | —CON(CH₃)(OCHCHCH₃) | —Ph-o-OCF₃ | H | 3-SCH₂CH₃ | Cx | 1 |
| —NH₂ | —CON(-c-C₃H₅)(OCH₂Ph) | —Ph-m-CN | 7-(CH₂)₂NH₂ | H | Ph | 1 |
| —NH₂ | —CON(Ph-p-CH₃)(OH) | —Ph-p-CH₂CH₃OH | H | H | Ph | 1 |
| NH(CH₂)₄CH₃ | —CON(C₂H₄Ph-m-OCH₃)(OCH₃) | —Ph-m-Ph-o-CH₃ | 7-(CH₂)₃Ph | H | Cx | 1 |
| —NH₂ | —CONH(OPh-p-CH₂CHCHCH₃) | —Ph-o-CH₂S | H | H | Ph | 2 |
| —N(CH₃)₂ | —CON(Ph)(OCH₂Ph-o-CHCHCH₃) | —Ph-p-CH₃Ph | H | 2-Br | Ph | 1 |
| —NH₂ | —CONH(I-c-C₆H₉) | —Ph-m-Ph | 8-OCH₃ | H | Cx | 1 |
| —NH₂ | —CON(CH₂CHCHCH₃)(OCH₂CH₃) | —Ph | —Br | H | Cx | 1 |
| —NH(CH₂CH₃) | —CON(CH₂CH₂Ph-o-CHCHCH₃) (O-c-C₅H₉) | —Ph-p-OCF₃ | 8-Cl | H | Cx | 1 |
| —NH₂ | —CON(Ph-p-Ph)(O—CH₂CH₂CH₂CH₃) | —Ph | 6-CH₂CH₂CH₃ | H | Ph | 1 |
| —NHNH(CH₂)₂CH₃ | —CONH(O—Ph-m-Cl) | —Ph-m-OCH₂CH₃ | 7-Ph | H | Ph | 1 |
| —NH₂ | —CON(CH₂CH₂CH₂CH₃)(O—Ph—OCH₃) | Ph | 6-CH₂Ph | H | Cx | 1 |
| —NH₂ | [tetrazole with CH₃] | —Ph-m-OPh-p-CH₃ | 7-CH₂Ph-p-CH₂Ph | H | Ph | 2 |
| —NH₂ | [tetrazole with CH₃Ph] | —Ph-o-OH | H | H | Ph | 1 |
| —NH₂ | [triazole with H] | Ph | H | H | Ph | 1 |
| —NH₂ | [tetrazole with H] | Ph | H | H | Cx | 3 |
| —NH₂ | [tetrazole with CH₃Ph] | Ph | 6-CH₂P-m-Ph-p-CH₃ | H | Ph | 1 |
| —CON(CH₂CH₂CH₃)₂ | —CON(CH₃)(OH) | —(CH₂CH₂CH₂CH₃) | 7-Ph-p-CF₃ | H | Cx | 1 |
| —NH₂ | —CON(CH₃)(OH) | —Ph | -furyl | H | Ph | 1 |
| —NH₂ | —CON(CH₃)(OH) | Pyridyl | H | 2-c-(C₃—H₅) | Ph | 1 |

TABLE 1-continued

| $R^1$ | $R^{2'}$ | $R^{20}$ | $R^{3'}$ | $R^{21}$ | Z | j |
|---|---|---|---|---|---|---|
| —$NH_2$ | —$CON(CH_2)(OH)$ | —Ph—O—Br-p-Ph-p-$CH_2$Ph | H | 1-Ph-p-$CH_3$ | Cx | 1 |
| —$NH_2$ | —$CON(CH_3)(OH)$ | Ph-o-OPh | 7-$CH_2OCHCHCH_3$ | H | Cx | 1 |
| —$NH_2$ | —$CON(CH_3)(OH)$ | —Ph-o-$OCF_3$ | 7-$CH_2CN$ | H | Ph | 1 |
| —$NH_2$ | —$CON(CH_3)(OH)$ | Ph | 6-thio-pohenyl | H | Ph | 1 |
| —$NH_2$ | —$CON(CH_3(OH)$ | Ph | 7-$(CH_2)_4CONH_2$ | H | Cx | 1 |
| —$NHN(CH_3)_2$ | —$CON(CH_3)(OH)$ | Ph | H | 2-$OCH_3$ | Ph | 1 |
| —$NHNH(CH_2CH_3)$ | —$CON(CH_3)(OH)$ | Ph | H | 2-Ph | Cx | 2 |
| —$NH_2$ | —$CON(CH_3)(OH)$ | Ph | H | 1-Ph-o-Cl | CX | 1 |
| —$NH_2$ | —$CON(CH_3)(OH)$ | Ph | H | 2-Cl | Ph | 1 |
| —$NH_2$ | —$CON(CH_3)(OH)$ | Ph | H | 2-c-$(C_3—H_5)$ | Ph | 1 |

Key:
"-c-" means cyclic
"Ph" means phenyl
"-o-" means ortho
"-m-" means meta
"-p-" means para
"Cx" means cyclohexyl
For $R^3$ and $R^{21}$, the number preceding the substituent means the position the sunstituent is attached to the tricyclic ring.

Synthesis Methods

Compounds of formula I can be prepared as described in scheme I below:

Scheme I

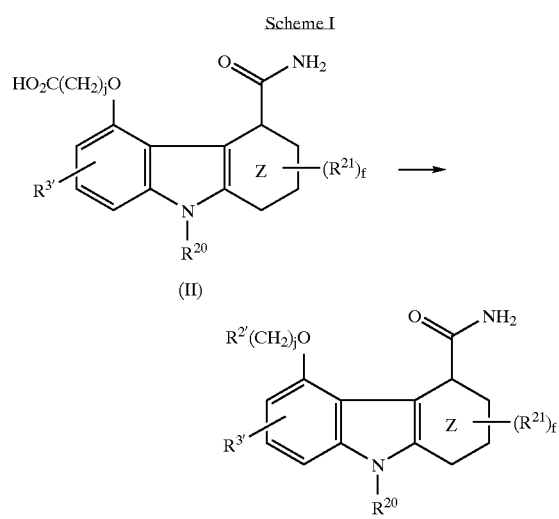

In general, the reaction is conducted by contacting a hydroxy amine of the formula $HN(R^{40} R^{41})$; where $R^{40}$ is selected from —OH, —$O(C_1-C_8)$alkyl, —$O(C_2-C_8)$alkenyl, —$O(C_3-C_8)$cycloalkyl, —O(aryl) and —$O(C_1-C_8)$alkylaryl; and $R^{41}$ is selected from hydrogen, —$(C_1-C_8)$alkyl, —$(C_2-C_8)$alkenyl, —$(C_3-C_8)$cycloalkyl, aryl and —$(C_1-C_8)$alkylaryl; with a compound of formula II in the presence of a base and a coupling reagent. In general, a wide variety of solvents can be employed including chloroform, methylene chloride, tetrahydrofuran (THF), acetonitrile, dimethylformamide(DMF) and dioxane. Couplings can even be done in aqueous solutions using water soluble carbodiimides.

Preferably, the reaction is conducted in a polar solvent such as DMF or water; or in a polar co-solvent mixture such as water/THF or water/DMF/THF.

Ambient temperatures are preferred in the range of from about 0° to 40° C.

Suitable bases include tertiary amines or pyridine derivatives such as collidine.

Examples of suitable coupling reagents include but are not limited to benzotriazol-1-gloxytris-(dimethylamino) phosphonium hexafluorophosphate, 1-hydroxy-7-azabenzotriazole, O-(7-azabenzotriazol-1-yl)-N,N,N'N'-tetramethyluronium, 1-hydroxy benzotriazole, 1-hydroxybenzotriazole hydrate, O-benzotriazol-1-yl-N,N,N',N'-bis(tetramethylene)uronium hexafluorophosphate, O-benzotriazole-1-yl-N,N,N',N'-tetramethyluronium hexafluorophosphate, benzotriazol-1-yl oxytris (dimethylamino)phosphonium hexaflurophosphate, N-hydroxysuccinimide, 1,1'-carbonyldiimidazole, 1-cyclohexyl-3-(2-morpholinolthyl)carbodiimide metho-p-toluenesulfonate, 1,3-dicyclohexylcarbodiimide (DCC), 1,3-diisopropylcarbodiimide (DIC), 2-ethoxy-1-ethoxycarbonyl-1,2-dihydroquinoline (EEDQ), or 2-isobutoxy-1-isobutoxycarbonyl-1,2-dihydroquinoline (IIDQ).

Starting materials of formula II may be prepared as described in U.S. application Ser. No. 09/062,328 or PCT Application No. PCTUS99/08261 herein incorporated by reference in their entirety.

The following list of abreviations are used in the Examples and Preparations.

EtOAc=ethyl acetate
DMF=dimethyl formamide
THF=tetrahydrofuran
$Et_2O$=diethyl ether
EtOH=ethanol
CELITE=diatomaceous earth MeOH=methanol
Rh/Al$_2$O$_3$=rhodium on alumina
DDQ=2,3-dichloro-5,6-dicyano-1,4-benzoquinone
TLC=thin layer chromatography
NH$_4$OAc=ammonium acetate
Olivetol=5-pentylresorcinol
Pd(OAc)$_2$=palladium diacetate
TRITON B=Benzyltrimethylammonium hydroxide The following Preparations and Examples further illustrate the preparation of the compounds of this invention. The Examples are illustrative only and are not intended to limit the scope of the invention in any way.

Preparation 1

{9-[(phenyl)methyl]-5-carbamoylcarbazol-4-yl}oxyacetic acid, sodium salt

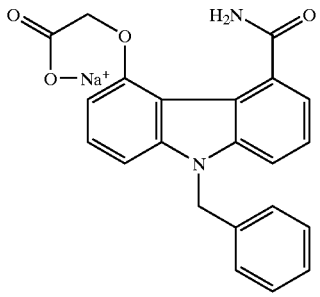

A. 9-[(Phenyl)methyl]-5-carbomethoxy-1,2-dihydrocarbazol-4(3H)-one

A suspension of 5-carbomethoxy-1,2-dihydro-9H-carbazol-4(3H)-one (300 mg, 1.23 mM), benzyl bromide (210 mg, 1.23 mM), and potassium carbonate (170 mg, 1.23 mM) in 15 mL DMF was stirred at room temperature for 6 hours. The mixture was diluted with 80 mL H$_2$O and chilled in the refrigerator. The resultant white precipitate was collected by filtration, washed with H$_2$O, and dried in vacuo to afford 325 mg (79%) of the 9-[(phenyl)methyl]-5-carbomethoxy-1,2-dihydrocarbazol-4(3H)-one as a white solid. $^1$H NMR (DMSO-d6) δ 7.7 (dd, 1H, J=1 and 8 Hz), 7.45–7.0 (m, 7H), 5.6 (s, 2H), 3.8 (s, 3H), 3.05 (t, 2H, J=6 Hz), 2.5 (t, 2H, J=6 Hz), and 2.2 (m, 2H). IR (KBr, cm$^{-1}$) 3421, 1726, 1676, 1636, 1473, 1450, 1435, 1288, 1122, 764, 745, and 706. MS (ES) m/e 334.

Elemental Analyses for C$_{24}$H$_{19}$NO$_3$: Calculated: C, 75.68; H, 5.71; N, 4.20. Found: C, 70.85; H, 5.53; N, 4.49.

B. 9-[(Phenyl)methyl]-4-hydroxy-5-carbomethoxy carbazole (a) A solution of the 9-[(phenyl)methyl]-5-carbomethoxy-1,2-dihydrocarbazol-4(3H)-one (1.5 g, 4.5 mM) and 2,3-dichloro-5,6-dicyano-1,4-benzoquinone (1.12 g, 5.0 mM) in 25 mL of toluene was stirred between 80–90° C. for 6 hours. The mixture was purified directly by column chromatography on silica gel (elution with methylene chloride/ethyl acetate) to afford 420 mg (28%) of the 9-[(phenyl)methyl]-4-hydroxy-5-carbomethoxy carbazole as a yellow solid. $^1$H NMR (DMSO-d6) δ 10.25 (s, 1H), 7.7 (d, 1H, J=8 Hz), 7.4 (t, 1H, J=8 Hz), 7.4–7.0 (m, 8H), 6.6 (d, 1H, J=8 Hz), 5.6 (s, 2H), and 3.8 (s, 3H). IR (CHCl$_3$, cm$^{-1}$) 1723, 1685, 1621, 1597, 1568, 1496, 1453, 1442, 1392, 1286, 1267, 1156, and 1138. MS (ES) m/e 330, 332.

Elemental Analyses for C$_{21}$H$_{17}$NO$_3$: Calculated: C, 76.13; H, 5.14; N, 4.23. Found: C, 75.90; H, 5.20; N, 4.46.

Alternately sub-titled compound may be prepared as described in (b), below.

(b) To a solution of the 9-[(phenyl)methyl]-5-carbomethoxy-1,2-dihydrocarbazol-4(3H)-one (2.87 g, 8.61 mM) in 29 ml dioxane was added 60% sodium hydride in mineral oil (0.79 g, 19.8 mM). The reaction was stirred 8 minutes, then methyl benzenesulfinate (1.80 ml, 13.8 mM) was added. The reaction was stirred an additional 1.5 hours, then diluted with 43 ml dioxane and 1.13 ml acetic acid. The mixture was refluxed 1 hour, diluted with ethyl acetate, and extracted with saturated NaHCO$_3$ two times, then with brine. After drying (NaSO$_4$), evaporation in vacuo afforded 4.90 g. The mixture was purified by column chromatography on silica gel (elution with toluene/methylene chloride) to afford 2.31 g (81%) of the 9-[(phenyl)methyl]-4-hydroxy-5-carbomethoxy carbazole. $^1$H NMR (DMSO-d6) δ 10.25 (s, 1H), 7.7 (d, 1H, J=8 Hz), 7.4 (t, 1H, J=8 Hz), 7.4–7.0 (m, 8H), 6.6 (d, 1H, J=8 Hz), 5.6 (s, 2H), and 3.8 (s, 3H). IR (CHCl$_3$, cm$^{-1}$) 1723, 1685, 1621, 1597, 1568, 1496, 1453, 1442, 1392, 1286, 1267, 1156, and 1138. MS (ES) m/e 330, 332.

Elemental Analyses for C$_{21}$H$_{17}$NO$_3$: Calculated: C, 76.13; H, 5.14; N, 4.23. Found: C, 75.90; H, 5.20; N, 4.46.

C. 9-[(Phenyl)methyl]-4-hydroxy-5-carbamoyl carbazole

A solution of the 9-[(phenyl)methyl]-4-hydroxy-5-Carbomethoxy carbazole (200 mg, 0.6 mM) in 4 mL MeOH and 40 mL concentrated aqueous ammonium hydroxide was sonicated for 30 hours at 40–50° C. The mixture was diluted with ethyl acetate and acidified to pH 1 with 5 N HCl. The aqueous layer was extracted three times with ethyl acetate. The combined organic extracts were washed with saturated brine, dried over magnesium sulfate, filtered, and concentrated. The residue was purified by column chromatography on silica gel (elution with gradient methylene chloride/ethyl acetate) to afford 50 mg (26%) of the 9-[(phenyl)methyl]-4-hydroxy-5-carbamoyl carbazole as a white solid. $^1$H NMR (DMSO-d6) δ 10.5 (s, 1H), 8.8 (br s, 1H), 8.4 (br s, 1H), 7.85 (dd, 1H, J=1 and 8 Hz), 7.5–7.1 (m, 9H), 6.6 (d, 1H, J=8 Hz), and 5.8 (s, 2H). IR (KBr, cm$^{-1}$) 3428, 3198, 3063, 1631, 1599, 1579, 1562, 1496, 1442, 1330, 1261, 1215, 775, and 697. MS (ES) m/e 315, 317.

Elemental Analyses for C$_{20}$H$_{16}$N$_2$O$_2$: Calculated: C, 75.95; H, 5.06; N, 8.86. Found: C, 74.88; H, 5.40; N, 7.78.

D. {9-[(Phenyl)methyl]-5-carbamoylcarbazol-4-yl}oxyacetic acid, methyl eater

40% Methanolic Triton B (0.11 mL, 0.24 mM) was added to a solution of the 9-[(phenyl)methyl]-4-hydroxy-5-carbamoyl carbazole (70 mg, 0.22 mM) in 20 mL DMF at 0° C. After 15 minutes, methyl bromoacetate (70 mg, 0.44 mM) was added and the resultant mixture stirred at room temperature for 5 hours. The mixture was diluted with ethyl acetate, washed with 1 N HCl, H$_2$O, and saturated brine, dried over magnesium sulfate, filtered, and concentrated. The residue was combined with the crude material derived from a similar run utilizing 45 mg (0.14 mM [0.36 mM total]) of 9-[(phenyl)methyl]-4-hydroxy-5-carbamoyl carbazole. The combined residues were purified by column chromatography on silica gel (elution with ethyl acetate) to afford 76 mg (54%) of the {9-[(phenyl)methyl]-5-carbamoylcarbazol-4-yl}oxyacetic acid, methyl ester as a white solid. $^1$H NMR (DMSO-d6) δ 7.65 (d, 1H, J=8 Hz), 7.5 (br s, 1H), 7.4–7.15 (m, 9H), 7.1 (d, 1H, J=8 Hz), 6.6 (d, 1H, J=8 Hz), 5.7 (s, 2H), 4.9 (s, 2H), and 3.75 (s, 3H). IR (KBr, cm$^{-1}$) 3367, 3200, 1760, 1643, 1579, 1496, 1452, 1427, 1216, 1157, 772, and 716. MS (FD) m/e 388.

Elemental Analyses for C$_{23}$H$_{20}$N$_2$O$_4$: Calculated: C, 71.13; H, 5.15; N, 7.22. Found: C, 70.77; H, 5.49; N, 6.79.

E. {9-[(Phenyl)methyl]-5-carbamoylcarbazol-4-yl}oxyacetic acid, sodium salt

A solution of the {9-[(phenyl)methyl]-5-carbamoylcarbazol-4-yl}oxyacetic acid, methyl ester (10.1 mg, 0.025 mM) and 0.025 mL (0.025 mM) of 1 N NaOH in 3 mL of ethanol was stirred for 16 hours at 25° C. The resultant white precipitate was collected by filtration, washed with a small amount of EtOH, then dried in vacuo to afford 7.1 mg (70%) of the {9-[(phenyl)methyl]-5-carbamoylcarbazol-4-yl}oxyacetic acid, sodium salt as a white powder. $^1$H NMR (DMSO-d6) δ 7.6 (d, 1H, J=8 Hz), 7.5–7.05 (m, 11H), 6.55 (d, 1H, J=8 Hz), 5.75 (s, 2H), and 4.3 (s, 2H). IR (KBr, cm$^{-1}$) 3471, 1657, 1615, 1591, 1496, 1453, 1412, 1330, 1272, and 1151. MS (ES) m/e 373, 375, 397.

Elemental Analyses for $C_{22}H_{17}N_2O_4Na$: Calculated; C, 66.67; H, 4.29; N, 7.07. Found: C, 66.75; H, 4.55; N, 6.83.

Preparation 2

[5-carbamoyl-2-pentyl-9-(phenylmethyl)carbazol-4-yl]oxyacetic acid

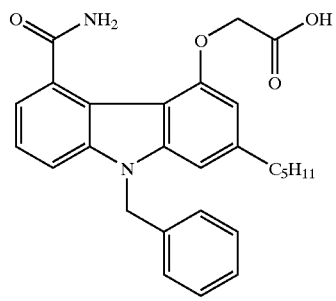

A. Preparation of a mixture of 5-pentylcyclohexa-1,3-dione and its enol isomer

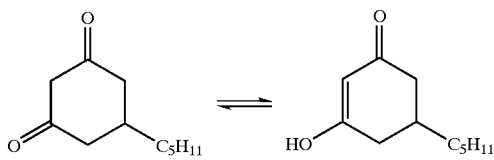

Sodium hydroxide (1.98 g, 49.5 mmol) was added to a stirred suspension of olivetol (7.20 g, 39.9 mmol) in THF (20 mL)/H$_2$O (20 mL) at ambient temperature under nitrogen atmosphere. The solution was stirred until it became a clear solution. The stir bar was removed before 5% Rh/Al$_2$O$_3$ (500 mg) was added to the solution. The mixture was then subject to hydrogenation condition under a 60 pounds per square inch hydrogen atmosphere in a Parr shaker for 17 hours. After filtration through CELITE, the filtrate was cooled to 0° C., then treated with 5 N HCl (10.9 mL). The mixture was evaporated in vacuo at 40° C. and the residue was chromatographed on silica (gradient 40–100% ethyl acetate in hexane, then 0–15% methanol in ethyl acetate) to give sub-titled compound (4.80 g, 66%) as a white solid mixture of keto/enol isomers in a 3:2 ratio. mp 68.5–69.5° C.; IR (KBr) 3200–2400 (br), 1610, 1542 cm$^{-1}$; $^1$H NMR (CDCl$_3$) δ 0.88 (br t, J=6.6 Hz, 3H, —CH$_3$), 3.38 (s, 2H, —CH$_2$— of keto isomer), 4.13 (s, 1H, =CH— of enol isomer), 8.90 (br s, 1H, —OH); ESIMS m/e 183 (M$^+$+1);

Elemental Analyses for $C_{11}H_{18}O_2$: Calculated: C, 72.49; H, 9.95. Found: C, 72.72; H, 9.95.

B. Preparation of a mixture of 5-hydroxymethyl)clohexa-1, 3-dione and its enol isomer

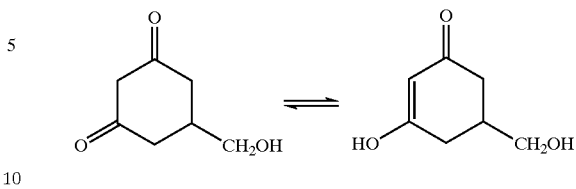

Following the experimental procedure as described in part A, above synthesis of subtitled compound was obtained in a 75% yield. IR (KBr) 3547, 3453 (br), 1633, 1580 cm$^{-1}$; $^1$H NMR (DMSO-d$_6$) δ 1.90–2.30 (m, 5H), 3.30 (brs, 2H, —CH$_2$O—), 4.61 (br s, 1H, —OH), 5.13 (s, 1H), 10.94 (s, 1H, —OH); ESIMS m/e 143 (M$^+$+1);

Elemental Analyses for $C_7H_{10}O_3$: Calculated: C, 59.14; H, 7.09. Found: C, 59.44; H, 7.08.

C. 3-(2-bromo-3-carbomethoxyanilino)-5-pentylcyclohex-2-en-1-one

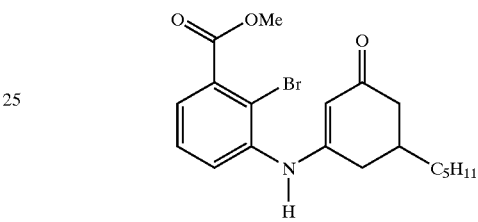

A stirred mixture of methyl-3-amino-2-bromobenzoate prepared as described in Preparation 4B(a) or (b) below (5.12 g, 22.3 mmol) and the compound of Part A (4.06 g, 22.3 mmol) was heated in an oil bath at 150° C. for 1.4 hours under a positive nitrogen pressure to continuously remove the water vapor. At ambient temperature, the mixture was chromatographed on silica (gradient 30–100% ethyl acetate in hexane) to provide subtitled compound (6.06 g, 69%) as a white solid. mp 132.0–134.0° C.; IR (KBr) 3220 (br), 1726, 1580 cm$^{-1}$; $^1$H NMR (CDCl$_3$) δ 0.90 (br t, J=6.6 Hz, 3H, —CH$_3$), 1.25–1.45 (m, 8H), 2.05–2.27 (m, 2H), 2.35–2.57 (m, 3H), 3.94 (s, 3H, —OCH$_3$), 5.57 (s, 1H, =CH—), 6.44 (br s, 1H, —NH), 7.35 (t, J=6.8 Hz, 1H), 7.53 (d, J=6.8 Hz, 2H); ESIMS m/e 394 (M$^+$+1, $^{79}$Br), 396 (M$^+$+1, $^{81}$Br).

D. 5-carbomethoxy-1,2-dihydro-2-pentyl-9H-carbazol-4 (3H)-one

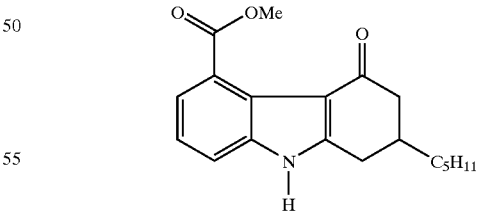

Triethylamine (2.09 mL, 15.0 mmol) was added to a stirred suspension of the compound of part C, above (3.94 g, 10.0 mmol), Pd(OAc)$_2$ (338 mg, 1.50 mmol), and tri-o-tolylphosphine (914 mg, 3.00 mmol) in acetonitrile (40 mL) at ambient temperature under nitrogen atmosphere. The resultant mixture was then heated in an oil bath at 85° C. for 1 hour. The mixture was evaporated in vacuo at 35° C. and the residue was chromatographed on silica (gradient 20–100% ethyl acetate in hexane) to give subtitled compound (2.45 g, 78%) as a white solid. mp 116.0–117.5° C.; IR (KBr) 3379 (br), 3180 (Br), 1725, 1627 cm$^{-1}$; $^1$H NMR (CDCl$_3$) δ 0.89 (br t, J=6.6 Hz, 3H, —CH$_3$), 1.20–1.47 (m, 8H), 2.20–2.32 (m, 2H), 2.50–2.67 (m, 2H), 2.92–3.05 (m, 1H), 4.02 (s, 3H, —OCH$_3$), 7.18–7.26 (m, 1H), 7.35–7.43 (m, 2H), 9.20–9.42 (br s, 1H, —NH); ESIMS m/e 314 (M$^+$+1).

Elemental Analyses for C$_{19}$H$_{23}$NO$_3$: Calculated: C, 72.82; H, 7.40; N, 4.47. Found: C, 72.59; H, 7.43; N, 4.51.

E. 5-carbomethoxy-1,2-dihydro-2-pentyl-9-(phenylmethyl)carbazol-4(3H)-one

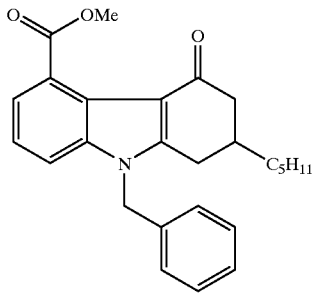

Benzylbromide (1.25 mL, 10.5 mmol) was added to a stirred suspension of the compound of part D (3.00 g, 9.57 mmol) and potassium carbonate (1.98 g, 14.4 mmol) in anhydrous DMF (30 mL) under nitrogen atmosphere. The resultant mixture was stirred for 5 hours. The mixture was evaporated in vacuo at 40° C. and the residue was chromatographed on silica (gradient 10–60% ethyl acetate in hexane) to give subtitled compound (3.28 g, 85%) as a white solid. mp 119.0–120.5° C.; IR (KBr) 1723, 1650 cm$^{-1}$; $^1$H NMR (CDCl$_3$) δ 0.87 (br t, J=6.6 Hz, 3H, —CH$_3$), 1.23–1.52 (m, 8H), 2.25–2.40 (m, 2H), 2.47–2.57 (m, 1H), 2.69 (d, J=12.8 Hz, 1H), 2.99 (dd, J=16.6, 3.6 Hz, 1H), 4.05 (s, 3H, —OCH$_3$), 5.36 (s, 2H), 6.98–7.02 (m, 2H), 7.20–7.40 (m, 6H); ESIMS m/e 404 (M$^+$+1).

F. 5-carbomethoxy-4-hydroxy-2-pentyl-9-(phenylmethyl)carbazole

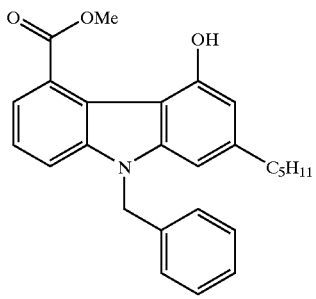

(a) from DDQ oxidation: DDQ (563 mg, 2.48 mmol) was added to a stirred suspension of the compound of part E, above (1.00 g, 2.48 mmol) in anhydrous toluene (30 mL) under nitrogen atmosphere. The resultant mixture was heated to reflux for 25 minutes. At ambient temperature, the mixture was subject to chromatographic purification on silica (gradient 0–30% ethyl acetate in toluene) to give subtitled compound (290 mg, 29%) as a yellow solid (310 mg, 31%).

(b) from benzenesulfinate elimination: Sodium hydride (60% in oil, 192 mg, 4.80 mmol) was added to a stirred solution of the compound of part E, above (807 mg, 2.00 mmol) and methyl benzenesulfinate (375 mg, 2.40 mmol) in anhydrous 1,4-dioxane (10 mL) under nitrogen atmosphere. The mixture was heated in an oil bath at 50° C. for 2 hours 15 minutes. After dilution with additional 15 mL 1,4-dioxane, the mixture was treated with acetic acid (0.343 mL, 6.00 mmol) and the resultant suspension was heated to reflux for 40 minutes. The mixture was evaporated in vacuo and the residue was chromatographed on silica (gradient 0–5% ethyl acetate in toluene) to afford subtitled compound (690 mg, 86%) as a yellow solid. mp 130.0–132.0° C.; IR (KBr) 3200 (br), 1686 cm$^{-1}$; $^1$H NMR (CDCl$_3$) δ 0.87 (br t, J=6.6 Hz, 3H, —CH$_3$), 1.25–1.38 (m, 4H), 1.60–1.75 (m, 2H), 2.69 (t, J=7.7 Hz, 2H), 4.10 (s, 3H, —OCH$_3$), 5.52 (s, 2H), 6.71 (s, 1H), 6.76 (s, 1H), 7.09–7.11 (m, 2H), 7.20–7.30 (m, 3H), 7.37 (t, J=8.0 Hz, 1H), 7.55 (d, J=8.0 Hz, 1H), 7.97 (d, J=8.0 Hz, 1H), 10.43 (s, 1H, —OH); ESIMS m/e 402 (M$^+$+1).

Elemental Analyses for C$_{26}$H$_{27}$NO$_3$∘0.2 (C$_7$H$_8$): Calculated: C, 78.37; H, 6.86; N, 3.34. Found: C, 78.48; H, 6.68; N, 3.53.

G. 5-carbamoyl-4-hydroxy-2-pentyl-9-(phenylmethyl)carbazole

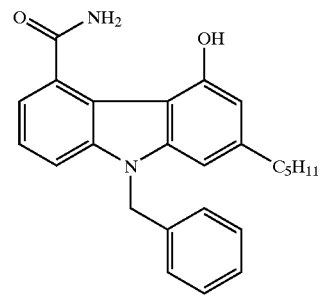

Ammonia was bubbled through a stirred suspension of the compund of part F, above (590 mg, 1.47 mmol) in ammonia water (50 mL)/THF (10 mL) at −25° C. for 5 minutes in a pressure bottle. The bottle was screw-capped before the is mixture was allowed to stir at ambient temperature for 3 days. After cooling to −25° C., the screw cap was removed and the mixture was allowed to stir at ambient temperature for 10 minutes. After concentration, the residue was subject to chromatographic purification on silica (gradient 0–40% tetrahydrofuran in toluene) to recover the compound of part F (160 mg, 27%) and obtain the desired subtitled product (397 mg, 70%) as a yellowish solid. IR (KBr) 3437, 3200 (br), 1633, 1601 cm$^{-1}$; $^1$H NMR (CDCl$_3$) δ 0.86 (br t, J=6.6 Hz, 3H, —CH$_3$), 1.22–1.38 (m, 4H), 1.60–1.75 (m, 2H), 2.69 (t, J=7.7 Hz, 2H), 5.52 (s, 2H), 6.16 (s, 1H, —NH), 6.53 (s, 1H, —NH), 6.72 (s, 1H), 6.76 (s, 1H), 7.07–7.11 (m, 2H), 7.23–7.30 (m, 3H), 7.35 (t, J=7.7 Hz, 1H), 7.43 (d, J=7.7 Hz, 1H), 7.48 (d, J=7.7 Hz, 1H), 9.80 (s, 1H, —OH); ESIMS m/e 387 (M$^+$+1);

Elemental Analyses for C$_{25}$H$_{26}$N$_2$O$_2$: Calculated: C, 77.69; H, 6.78; N, 7.25. Found: C, 77.69; H, 6.63; N, 7.15.

H. [5-carbamoyl-2-pentyl-9-(phenylmethyl)carbazol-4-yl]oxyacetic acid, methyl ester

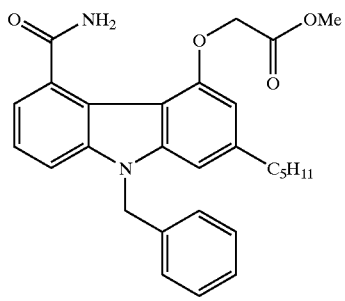

Methyl bromoacetate (48.0 mg, 0.314 mmol) was added to a stirred suspension of the compound of part G, above (110 mg, 0.285 mmol) and cesium carbonate (186 mg, 0.570 mmol) in anhydrous DMF (2 mL) at ambient temperature under nitrogen atmosphere. The resultant mixture was stirred for 1 hour. After concentration in vacuo at 40° C., the residue was chromatographed on silica (gradient 10–60% tetrahydrofuran in toluene) to give subtitled product (115 mg, 88%) as a white solid. mp 195.0–196.0° C.; IR (KBr) 3365 (br), 3157 (br), 1758, 1640 cm$^{-1}$; $^1$H NMR (CDCl$_3$) δ 0.87 (br t, J=6.6 Hz, 3H, —CH$_3$), 1.22–1.35 (m, 4H), 1.58–1.70 (m, 2H), 2.69 (t, J=7.6 Hz, 2H), 3.84 (s, 3H, —OCH$_3$), 4.89 (s, 2H, —OCH$_2$—), 5.50 (s, 2H, —NCH$_2$—), 5.95 (br s, 1H, —NH), 6.08 (br s, 1H, —NH), 6.41 (s, 1H), 6.85 (s, 1H), 7.07–7.11 (m, 2H), 7.23–7.40 (m, 6H); ESIMS m/e 459 (M$^+$+1);

Elemental Analyses for C$_{28}$H$_{30}$N$_2$O$_4$: Calculated: C, 73.34; H, 6.59; N, 6.11. Found: C, 73.56; H, 6.43; N, 6.25.

I. [5-carbamoyl-2-pentyl-9-(phenylmethyl)carbazol-4-yl]oxyacetic acid

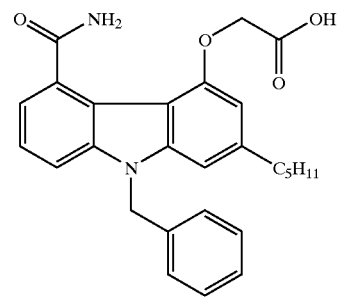

Lithium hydroxide (4.17 N, 86.3 mL, 0.360 mmol) was added to a stirred suspension of the compound of part H, above (110 mg, 0.240 mmol) in THF (2 mL)/CH$_3$OH (0.3 mL)/H$_2$O (0.3 mL). The resultant mixture was stirred in an oil bath at 55° C. for 30 minutes to form a white suspension. Five milliliter of THF was added to the suspension before it was treated with 5 N HCl (96.0 mL, 0.480 mmol) to become a clear solution. After concentration, the white solid was resuspended in THF (0.5 mL)/H$_2$O (5 mL), sonicated, filtered, and dried to give the subtitled compound (106 mg, 99%) as a white solid. IR (KBr) 3458 (br), 3500–3100 (br), 1656, 1620 cm$^{-1}$; $^1$H NMR (DMSO-d$_6$) δ 0.80 (br t, J=6.6 Hz, 3H, —CH$_3$), 1.18–1.30 (m, 4H), 1.50–1.62 (m, 2H), 2.61 (br t, J=7.3 Hz, 2H), 4.55 (s, 2H, —OCH$_2$—), 5.60 (s, 2H, —NCH$_2$—), 6.40 (s, 1H), 6.95–7.32 (m, 9H), 7.51 (d, J=8.0 Hz, 1H), 7.70 (br s, 1H, —NH); ESIMS m/e 445 (M$^+$+1)

Preparation 3

[5-carbamoyl-9-(phenylmethyl)-2-(2-thienyl)carbazol-4-yl]oxyacetic acid

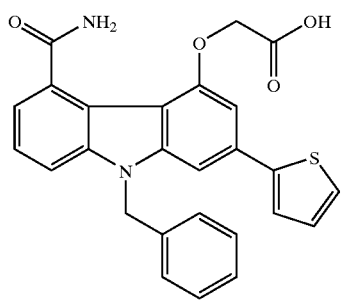

A. 3-(2-bromo-3-carbomethoxyanilino)-5-(2-thienyl)cyclohex-2-en-1-one

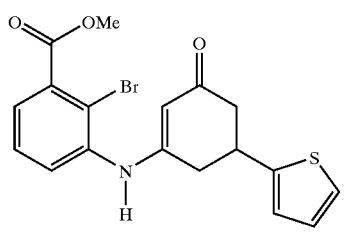

Prepared in 59% yield by the method of Preparation 2C.

$^1$H-NMR (CDCl$_3$): δ 2.63 (dd, J=16.5, 118. Hz, 1H), 2.78–2.96 (m, 3H), 3.71–3.80 (m, 1H), 3.94 (s, 3H), 5.61 (s, 1H), 6.23 (br s, 1H), 6.93 (d, J=3.5 Hz, 1H), 6.97–6.99 (m, 1H), 7.21 (d, J=5.2 Hz, 1H), 7.34 (br t, J=7.8 Hz, 1H), 7.55 (d, J=7.8 Hz, 2H).

B. 5-carbomethoxy-1,2-dihydro-2-(2-thienyl)-9H-carbazol-4(3H)-one

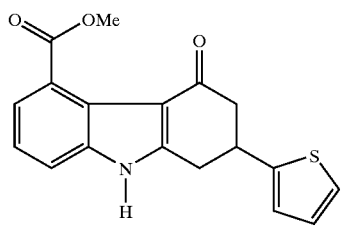

Prepared in 85% yield by the method of Preparation 2D.

$^1$H-NMR (CDCl$_3$): δ 2.73 (dd, J=16.3, 11.8 Hz, 1H), 2.91 (dd, J=16.4, 4.0 Hz, 1H), 3.03 (dd, J=16.6, 10.8 Hz, 1H), 3.24 (dd, J=16.6, 4.5 Hz, 1H), 3.75–3.78 (m, 1H), 4.03 (s, 3H), 6.88 (br s, 1H), 6.93–6.96 (m, 1H), 7.17 (d, J=5.0 Hz, 1H), 7.22–7.26 (m, 1H), 7.36 (d, J=7.4 Hz, 1H), 7.40 (d, J=8.0 Hz, 1H), 9.17 (br s, 1H).

C. 5-carbomethoxy-1,2-dihydro-9-(phenylmethyl)-2-(2-thienyl)carbazol-4(3H)-one

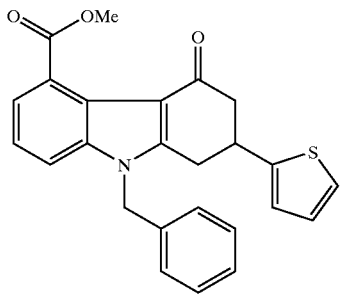

Prepared in 88% yield by the method of Preparation 2E. ¹H-NMR (CDCl₃): δ 2.84 (dd, J=16.5, 11.6 Hz, 1H), 2.97–3.10 (m, 2H), 3.34 (dd, J=16.5, 4.5 Hz, 1H), 3.89–3.96 (m, 1H), 4.06 (s, 3H), 5.38 (s, 2H), 6.89–7.00 (m, 4H), 7.18 (d, J=5.3 Hz, 1H), 7.25–7.41 (m, 6H).

D. 5-carbomethoxy-4-hydroxy-9-(phenylmethyl)-2-(2-thienyl)carbazole

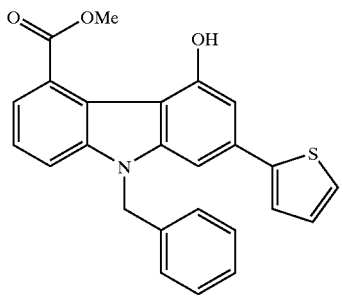

Prepared in 76% yield by the method (b) of Preparation 2F. ¹H-NMR (CDCl₃): δ 4.11 (s, 3H), 5.55 (s, 2H), 7.07–7.12 (m, 3H), 7.16 (s, 2H), 7.24–7.30 (m, 4H), 7.37–7.42 (m, 2H), 7.56 (d, J=8.1 Hz, 1H), 8.01 (d, J=7.6 Hz, 1H).

E. 5-carbamoyl-4-hydroxy-9-(phenylmethyl)-2-(2-thienyl)carbazole

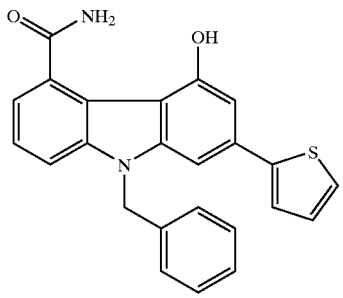

Prepared in 85% yield by the method of Preparation 2G. ¹H-NMR (DMSO-d₆): δ 5.73 (s, 2H), 6.87 (s, 1H), 7.08–7.26 (m, 6H), 7.41–7.56 (m, 5H), 7.76 (br t, J=4.5 Hz, 1H), 8.39 (s, 1H), 8.83 (s, 1H), 10.76 (s, 1H).

F. [5-carbamoyl-9-(phenylmethyl)-2-(2-thienyl)carbazol-4-yl]oxyacetic acid, methyl ester

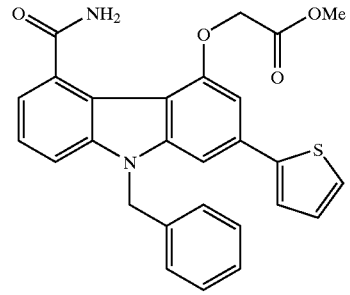

Prepared in 92% yield by the method of Preparation 2H. ¹H-NMR (DMSO-d₆): δ 3.70 (s, 3H), 4.99 (s, 2H), 5.71 (s, 2H), 6.85 (s, 1H), 7.04 (d, J=7.2 Hz, 1H), 7.11–7.26 (m, 7H), 7.35 (br t, J=7.7 Hz, 1H), 7.50–7.57 (m, 5H).

G. [5-carbamoyl-9-(phenylmethyl)-2-(2-thienyl)carbazol-4-yl]oxyacetic acid

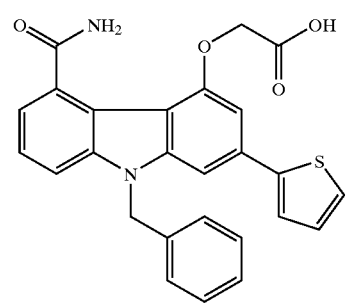

Prepared in 98% yield by the method of Preparation 2I. ¹H-NMR (DMSO-d₆): δ 4.90 (s, 2H), 5.72 (s, 2H), 6.85 (s, 1H), 7.04–7.26 (m, 7H), 7.33–7.38 (m, 2H), 7.50–7.59 (m, 4H), 7.71 (s, 1H), 12.99 (br s, 1H).

Preparation 4

5-Carbomethoxy-1,2-dihydro-9H-carbazol-4(3H)-one from 2-bromo-3-nitrobenzoic acid

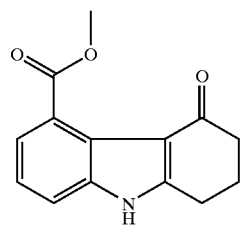

A. Methyl 2-bromo-3-nitrobenzoate

A solution of 2-bromo-3-nitrobenzoic acid (28.4 g, 115.0 mM), iodomethane (18.0 g, 127 mM), and potassium carbonate (19.0 g, 137.4 mM) in 100 mL DMF was stirred at room temperature for 72 hours. The mixture was poured into 1.5 liters of H₂O. The resultant precipitate was collected by filtration and dried in vacuo to afford 28.79 g (96%) of methyl 2-bromo-3-nitrobenzoate as a white solid. ¹H NMR (DMSO-d6) δ 8.3 (dd, 1H, J=1 and 8 Hz), 7.9 (dd, 1H, J=1 and 8 Hz), 7.7 (t, 1H, J=8 Hz), and 3.9 (s, 3H). IR (KBr, cm⁻¹) 2950, 1738, 1541, 1435, 1364, 1298, and 1142. MS (FD) m/e 259, 261.

Elemental Analyses for C₈H₆NO₄Br: Calculated: C, 36.95; H, 2.33; N, 5.39. Found: C, 37.14; H, 2.37; N, 5.45.

B. Methyl 2-bromo-3-aminobenzoate (a) Hydrogen gas was passed through a solution of methyl 2-bromo-3-nitrobenzoate (0.20 g, 0.77 mM) and 0.1 g of 3% sulfided platinum on carbon in 25 mL ethyl acetate for 24 hours at room temperature. The catalyst was removed by filtration through CELITE. Concentration of the filtrate afforded 0.175 g (99%) of methyl 2-bromo-3-aminobenzoate as a yellow oil. $^1$H NMR (CDCl$_3$) δ 7.15 (t, 1H, J=8 Hz), 7.1 (dd, 1H, J=1 and 8 Hz), 6.8 (dd, 1H, J=1 and 8 Hz), and 3.95 (s, 3H). IR (CHCl$_3$, cm$^{-1}$) 3550, 3380, 2980, 2900, 1729, 1613, 1465, 1451, 1434, 1324, 1266, and 1025. MS (FD) m/e 230, 232.

Elemental Analyses for C$_8$H$_8$NO$_2$Br: Calculated: C, 41.77; H, 3.51; N, 6.09. Found: C, 42.01; H, 3.29; N, 6.00.

Alternately, subtitled compound may be prepared as follows:

(b) A solution of stannous chloride (15.0 g, 76.1 mM) in 30 mL of concentrated hydrochloric acid was slowly added to a solution of methyl 2-bromo-3-nitrobenzoate (4.0 g, 15.4 mM) in 90 mL ethanol at 15–30° C. over 1 hour. The mixture was then heated at 50–60° C. for 15 minutes. The mixture was cooled to room temperature and made alkaline by slow addition of solid sodium hydroxide maintaining a temperature of 30–35° C. The resultant mixture was extracted three times with chloroform. The extracts were washed with brine, dried over sodium sulfate, filtered and concentrated to afford 3.51 g (99%) of methyl 2-bromo-3-aminobenzoate as a yellow oil, identical in all respects to the material derived via catalytic hydrogenation described above.

C. 3-(3-Carbomethoxy-2-bromoanilino)cyclohex-2-en-1-one

A mixture of methyl 2-bromo-3-aminobenzoate (13.2 g, 60.0 mM) and 1,3-cyclohexanedione (8.4 g, 75 mM) was heated at 125° C. under a stream of nitrogen for 4 hours. The resultant solid was purified by HPLC on silica gel (elution with methylene chloride/ethyl acetate) to afford 17.2 g (88%) of 3-(3-carbomethoxy-2-bromoanilino)cyclohex-2-en-1-one as a tan foam. $^1$H NMR (DMSO-d6) δ 8.75 (s, 1H), 7.6–7.4 (m, 3H), 4.65 (s, 1H), 3.85 (s, 3H), 2.6 (t, 2H, J=6 Hz), 2.15 (t, 2H, J=6 Hz), and 1.9 (m, 2H). IR (CHCl$_3$, cm$^{-1}$) 3400, 3004, 2954, 1732, 1607, 1588, 1573, 1513, 1464, 1436, 1412, 1308, 1249, 1177, and 1144. MS (ES) m/e 322, 324, 326.

Elemental Analyses for C$_{14}$H$_{14}$NO$_3$Br: Calculated: C, 51.85; H, 4.32; N, 4.32. Found: C, 53.60; H, 4.73; N, 4.09.

D. 5-Carbomethoxy-1,2-dihydro-9H-carbazol-4(3H)-one

A suspension of 3-(3-carbomethoxy-2-bromoanilino)cyclohex-2-en-1-one (15.8 g, 48.8 mM), palladium acetate (1.12 g, 5.0 mM), tri-o-tolylphosphine (3.1 g, 10.0 mM), and triethylamine (6.3 g, 62.0 mM) in 120 mL acetonitrile was heated at reflux for 8 hours. The solvent was removed in vacuo. The residue was dissolved in methylene chloride, washed twice with 1 N HCl, twice with H$_2$O, once with saturated brine, dried over anhydrous magnesium sulfate, filtered, and concentrated to afford 17 g of a light brown foam. Purification by HPLC on silica gel (elution with gradient methylene chloride/ethyl acetate) afforded 9.2 g (78%) of the 5-carbomethoxy-1,2-dihydro-9H-carbazol-4 (3H)-one as a yellow solid, identical with the material derived from 3-(3-carbomethoxy-2-chloroanilino)cyclohex-2-en-1-one, described above. $^1$H NMR (DMSO-d6) δ 7.5 (d, 1H, J=8 Hz), 7.25–7.1 (m, 2H), 5.7 (s, 1H), 3.8 (s, 3H), 2.95 (t, 2H, J=6 Hz), 2.4 (t, 2H, J=6 Hz), and 2.1 (m, 2H). MS (ES) m/e 242, 244.

EXAMPLE 1

[[5-Carbamoyl-9-(phenylmethyl)carbazol-4-yl]oxy]-N-(hydroxy)acetamide

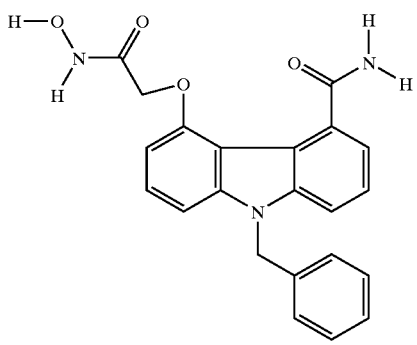

To a stirred suspension of the compound of Preparation 1E, free acid (0.093 g, 0.25 mmol) in 2 mL anhydrous DMF at ambient temperature was added collidine (0.036 mL, 0.27 mmol), O-(tert-butyldimethylsilyl) hydroxylamine (0.037 g, 0.25 mmol), and benzotriazol-1-yloxytris-(dimethylamino) phosphonium hexafluorophosphate (0.115 g, 0.261 mmol) sequentially. After 1.5 hours the reaction mixture was loaded directly onto a silica gel column packed with EtOAc and eluted with 10% THF in CH$_2$Cl$_2$. The desired fractions were concentrated in vacuo at 45° C. to near dryness then taken up in 2 mL THF. Two drops 1N HCl were added, the mixture was again concentrated in vacuo at 45° C. To the residue was added 1 mL THF, 1 mL distilled H$_2$O and 4 mL Et$_2$O followed by sonication to give a white precipitate, which was collected over a glass fritted funnel to give 0.043 g of title product as a white solid in 45% yield. $^1$H-NMR (DMSO-d6) δ 4.70 (s, 2H), 5.66 (s, 2H), 6.68 (d, J=7.9 Hz, 1H), 7.06–7.42 (m, 9H), 7.56 (s, 1H), 7.64 (d, J=8.1 Hz, 1H), 8.17 (s, 1H), 8.83 (s, 1H), 10.83 (s, 1H); ESIMS m/e 390 (M$^+$+1)

EXAMPLE 2

[[5-Carbamoyl-9-(phenylmethyl)carbazol-4-yl]oxy]-N-(methoxy)acetamide

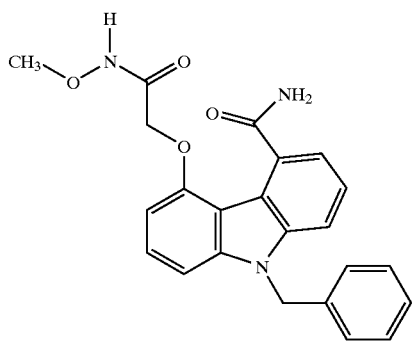

4-Methylmorpholine (0.308 mL, 2.80 mmol) was added to a stirred suspension of the compound of Preparation 1E, sodium salt of free acid (0.150 g, 0.401 mmol) and O-methyl hydroxylamine hydrochloride (0.0368 g, 0.441 mmol) in anhydrous DMF (2 mL) at ambient temperature to from a clear solution. Powdered benzotriazol-1-yloxytris-(dimethylamino) phosphonium hexafluorophosphate (0.195 g, 0.441 mmol) was added to the solution and the resultant mixture was stirred for 4 hours. After concentration in vacuo at 40° C., the residue was chromatographed on silica gel (gradient 0–3% $CH_3OH$ in $CH_2Cl_2$) to give title compound (0.123 g, 76%) as a white solid. IR(KBr) 3450, 3203, 1697 $cm^{-1}$; $^1H$-NMR (DMSO-$d_6$) δ 3.57 (s, 3H), 4.74 (s, 2H), 5.68 (s, 2H), 6.72 (d, J=8.0 Hz, 1H), 7.08–7.45 (m, 9H), 7.65 (s, 1H), 7.66 (d, J=8.4 Hz, 1H), 8.14(s, 1H), 11.45 (s, 1H); ESIMS m/e 404 ($M^+$+1).

EXAMPLE 3

[[5-Carbamoyl-9-(phenylmethyl)carbazol-4-yl]oxy]-N-(ethoxy)acetamide

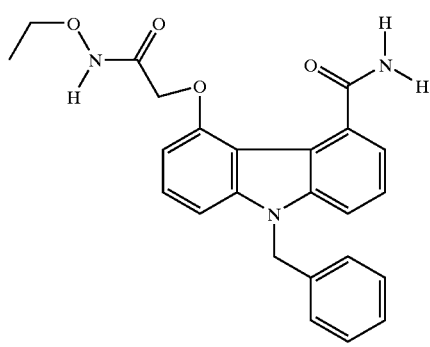

To a stirred suspension of the compound of Preparation 1E, sodium salt of free acid (0.093 g, 0.25 mmol) in 2 mL anhydrous DMF at ambient temperature was added collidine (0.069 mL, 0.52 mmol), O-ethyl hydroxylamine hydrochloride (0.024 g, 0.25 mmol), and benzotriazol-1-yloxytris-(dimethylamino)phosphonium hexafluorophosphate (0.115 g, 0.261 mmol) sequentially. After 1 hour, the reaction mixture was loaded directly onto a silica gel column packed with EtOAc and eluted with 10% THF in $CH_2Cl_2$. The desired fractions were concentrated in vacuo at 45° C. to about 2 mL then 2 mL distilled $H_2O$ and 5 mL $Et_2O$ were added. The mixture was sonicated giving a white precipitate, which was collected over a glass fritted funnel to give 0.056 g of title product as a white solid in 54% yield. $^1H$-NMR (DMSO-$d_6$) δ 0.99 (t, J=7.1 Hz, 3H), 3.72 (q, J=7.1 Hz, 2H), 4.72 (s, 2H), 5.66 (s, 2H), 6.68 (br d, J=7.8 Hz, 1H), 7.06–7.42 (m, 9H), 7.62–7.65 (m, 2H), 8.14(s, 1H), 11.28 (s, 1H); ESIMS m/e 418 ($M^+$+1).

EXAMPLE 4

[[5-Carbamoyl-9-(phenylmethyl)carbazol-4-yl]oxy]-N-[(phenylmethyl)oxy]acetamide

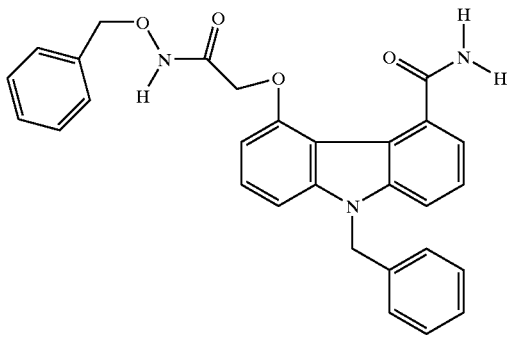

Following the experimental procedure as described in Example 2, and using a slight excess of o-benzyl hydroxylamine hydrochloride in place of O-methyl hydroxylamine hydrochloride, the title product was obtained as a white solid in 70% yield. $^1H$-NMR (DMSO-$d_6$) d 4.73 (br s, 4H), 5.67 (s, 2H), 6.69 (d, J=7.8 Hz, 1H), 7.08–7.42 (m, 14H), 7.56 (s, 1H), 7.64 (d, J=8.2 Hz, 1H), 8.10 (s, 1H), 11.46 (s, 1H); ESIMS m/e 480 ($M^+$+1).

EXAMPLE 5

[[5-Carbamoyl-9-(phenylmethyl)carbazol-4-yl]oxy]-N-(methoxy)-N-(methyl)acetamide

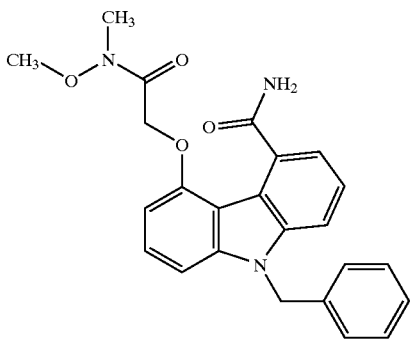

Following the experimental procedure as described in Example 2, and using a slight excess of O-methyl hydroxymethylamine hydrochloride in place of O-methyl hydroxylamine hydrochloride, the title product was obtained as a white solid in 88% yield. IR($CHCl_3$) 3500, 3400, 1679 $cm^{-1}$; $^1H$-NMR (DMSO-$d_6$) δ 3.18 (s, 3H), 3.81 (s, 3H), 5.05 (s, 2H), 5.68 (s, 2H), 6.53 (d, J=7.9 Hz, 1H), 7.05–7.42 (m, 10H), 7.50 (br s, 1H), 7.61 (d, J=8.2 Hz, 1H); ESIMS m/e 418 ($M^+$1).

EXAMPLE 6

[[5-Carbamoyl-9-(phenylmethyl)carbazol-4-yl]oxy]-N-(phenyloxy)acetamide

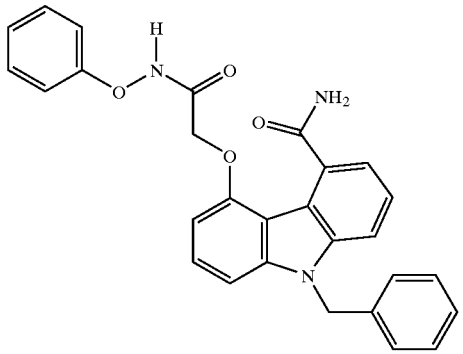

Following the experimental procedure as described in Example 2, and using O-phenyl hydroxylamine hydrochloride in place of O-methyl hydroxylamine hydrochloride, the title product was obtained as a white solid in 66% yield. IR(KBr) 3500, 3400, 3196, 1656 cm$^{-1}$; $^1$H-NMR (DMSO-d$_6$) δ 4.96 (s, 2H), 5.71 (s, 2H), 6.72 (d, J=7.7 Hz, 2H), 6.83 (d, J=8.0 Hz, 1H), 6.91 (t, J=7.2 Hz, 1H), 7.05–7.50 (m, 11H), 7.67 (d, J=8.4 Hz, 1H), 7.84 (s, 1H), 8.29 (s, 1H), 12.10 (s, 1H); ESIMS m/e 466 (M$^+$+1).

EXAMPLE 7

[[5-Carbamoyl-9-(phenylmethyl)-2-(thien-2-yl)carbazol-4-yl]oxy]-N-[(phenylmethyl)oxy]acetamide

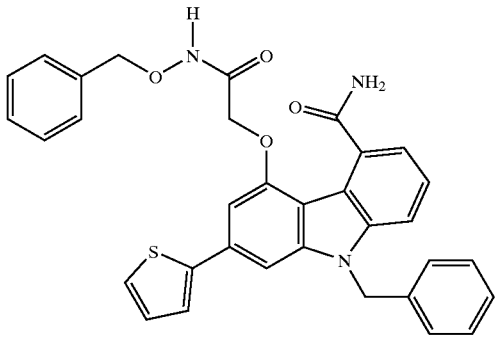

Following the experimental procedure as described in Example 2, and using O-benzyl hydroxylamine hydrochloride in place of O-methyl hydroxylamine hydrochloride, the title product was obtained from the compound of Preparation 3G as a white solid in 50% yield. IR(KBr) 3478, 3300, 3204, 1693, 1659 cm$^{-1}$; $^1$H-NMR (DMSO-d$_6$) □ 4.77 (s, 2H), 4.68 (s, 2H), 5.76 (s, 2H), 6.98 (s, 1H), 7.10–7.30 (m, 12H), 7.41 (t, J=7.5 Hz, 1H), 7.54–7.66 (m, 5H), 8.12 (s, 1H), 11.50 (s, 1H); ESIMS m/e 560 (M$^-$−1).

Elemental Analyses for $C_{33}H_{27}N_3O_4S \cdot H_2O$: Calculated: C, 68.38; H, 5.04; N, 7.25. Found: C, 68.49; H, 4.90; N, 7.25.

Therapeutic Use of Tricyclic Compounds

The compounds described herein are believed to achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, etc.

The method of the invention for inhibiting sPLA$_2$ mediated release of fatty acids comprises contacting sPLA$_2$ with an therapeutically effective amount of the compound of Formula (I) or its salt.

The compounds of the invention may be used in a method of treating a mammal (e.g., a human) to alleviate the pathological effects of sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease, apoptosis, stroke, cystic fibrosis, allergic rhinitis, acute bronchiolitis, chronic bronchiolitis, gout, spondylarthropathris, ankylosing spondylitis, Reiter's syndrome, psoriatic arthropathy, enterapathric spondylitis, Juvenile arthropathy or juvenile ankylosing spondylitis, Reactive arthropathy, infectious or post-infectious arthritis, gonoccocal arthritis, tuberculous arthritis, viral arthritis, fungal arthritis, syphilitic arthritis, Lyme disease, arthritis associated with "vasculitic syndromes", polyarteritis nodosa, hypersensitivity vasculitis, Luegenec's granulomatosis, polymyalgin rheumatica, joint cell arteritis, calcium crystal deposition arthropathris, pseudo gout, non-articular rheumatism, bursitis, tenosynomitis, epicondylitis (tennis elbow), carpal tunnel syndrome, repetitive use injury (typing), miscellaneous forms of arthritis, neuropathic joint disease (charco and joint), hemarthrosis (hemarthrosic), Henoch-Schonlein Purpura, hypertrophic osteoarthropathy, multicentric reticulohistiocytosis, arthritis associated with certain diseases, surcoilosis, hemochromatosis, sickle cell disease and other hemoglobinopathries, hyperlipoproteineimia, hypogammaglobulinemia, hyperparathyroidism, acromegaly, familial Mediterranean fever, Behat's Disease, systemic lupus erythrematosis, or relapsing polychondritis; and related diseases (preferably, sepsis, septic shock, adult respiratory distress syndrome, pancreatitis, trauma-induced shock, asthma, rheumatoid arthritis, osteoarthritis, acute bronchitis, chronic bronchitis, Inflammatory Bowel Disease) wherein the method comprises administering to the mammal a compound of formula (I) in a therapeutically effective amount. A "therapeutically effective" amount is an amount sufficient to inhibit sPLA$_2$ mediated release of fatty acid and to thereby inhibit or prevent the arachidonic acid cascade and its deleterious products. The therapeutic amount of compound of the invention needed to inhibit sPLA$_2$ may be readily determined by taking a sample of body fluid and assaying it for sPLA$_2$ content by conventional methods.

Throughout this document, the person or animal to be treated will be described as a "mammal", and it will be understood that the most preferred subject is a human. However it must be noted that the study of adverse conditions of the central nervous system in non-human animals is only now beginning, and that some instances of such treatments are coming into use. Accordingly, use of the present compounds in non-human animals is contemplated. It will be understood that the dosage ranges for other animals will necessarily be quite different from the doses administered to humans, and accordingly that the dosage ranges described be recalculated. For example, a small dog may be only $\frac{1}{10}^{th}$ of a typical human's size, and it will therefore be necessary for a much smaller dose to be used. The determination of an effective amount for a certain non-human animal is carried out in the same manner described below in the case of humans, and veterinarians are well accustomed to such determinations.

Pharmaceutical Formulations of the Invention

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention. By "pharmaceutically acceptable" it is meant the carrier, diluent or excipient must be compatible with the other ingredients of the formulation and not deleterious to the recipient thereof.

In general, the compounds of the invention are most desirably administered at a dose that will generally afford effective results without causing any serious side effects and can be administered either as a single unit dose, or if desired, the dosage may be divided into convenient subunits administered at suitable times throughout the day.

The specific dose of a compound administered according to this invention to obtain therapeutic or prophylactic effects will, of course, be determined by the particular circumstances surrounding the case, including, for example, the route of administration, the age, weight and response of the individual patient, the condition being treated and the severity of the patient's symptoms. Typical daily doses will contain a non-toxic dosage level of from about 0.01 mg/kg to about 50 mg/kg of body weight of an active compound of this invention.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more, according to the particular treatment involved. It may be appreciated that it may be necessary to make routine variations to the dosage depending on the age and condition of the patient. The dosage will also depend on the route of administration.

A "chronic" condition means a deteriorating condition of slow progress and long continuance. As such, it is treated when it is diagnosed and continued throughout the course of the disease. An "acute" condition is an exacerbation of short course followed by a period of remission. In an acute event, compound is administered at the onset of symptoms and discontinued when the symptoms disappear.

For example, pancreatitis, trauma-induced shock, bronchial asthma, allergic rhinitis and rheumatoid arthritis may occur as an acute event or a chronic event. Thus, the treatment of these conditions contemplates both acute and chronic forms. Septic shock and adult respiratory distress, on the other hand, are acute conditions treated when diagnosed.

The compound can be administered by a variety of routes including oral, aerosol, rectal, transdermal, subcutaneous, intravenous, intramuscular, and intranasal.

Pharmaceutical formulations of the invention are prepared by combining (e.g., mixing) a therapeutically effective amount of the compounds of the invention together with a pharmaceutically acceptable carrier or diluent therefor. The present pharmaceutical formulations are prepared by known procedures using well known and readily available ingredients.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

For the pharmaceutical formulations any suitable carrier known in the art can be used. In such a formulation, the carrier may be a solid, liquid, or mixture of a solid and a liquid. Solid form formulations include powders, tablets and capsules. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

In powders, the carrier is a finely divided solid which is in admixture with the finely divided active ingredient. In tablets, the active ingredient is mixed with a carrier having the necessary binding properties in suitable proportions and compacted in the shape and size desired. The powders and tablets preferably contain from about 1 to about 99 weight percent of the active ingredient which is the novel compound of this invention. Suitable solid carriers are magnesium carbonate, magnesium stearate, talc, sugar, lactose, pectin, dextrin, starch, gelatin, tragacanth, methyl cellulose, sodium carboxymethyl cellulose, low melting waxes, and cocoa butter.

Sterile liquid form formulations include suspensions, emulsions, syrups and elixirs. The active ingredient can be dissolved or suspended in a pharmaceutically acceptable carrier, such as sterile water, sterile organic solvent or a mixture of both. The active ingredient can often be dissolved in a suitable organic solvent, for instance aqueous propylene glycol. Other compositions can be made by dispersing the finely divided active ingredient in aqueous starch or sodium carboxymethyl cellulose solution or in a suitable oil.

The following pharmaceutical formulations 1 through 8 are illustrative only and are not intended to limit the scope of the invention in any way. "Active ingredient", refers to a compound according to Formula (I) or a pharmaceutically acceptable salt or solvate thereof.

Formulation 1
Hard gelatin capsules are prepared using the following ingredients:

| | Quantity (mg/capsule) |
|---|---|
| Compound of Example 1 | 250 |
| Starch, dried | 200 |
| Magnesium stearate | 10 |
| Total | 460 mg |

| Formulation 2 | |
|---|---|
| A tablet is prepared using the ingredients below: | |
| | Quantity (mg/tablet) |
| Compound of Example 2 | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

| Formulation 3 | |
|---|---|
| An aerosol solution is prepared containing the following components: | |
| | Weight |
| Compound of Example 3 | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

| Formulation 4 | |
|---|---|
| Tablets, each containing 60 mg of active ingredient, are made as follows: | |
| Compound of Example 4 | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

| Formulation 5 | |
|---|---|
| Capsules, each containing 80 mg of active ingredient, are made as follows: | |
| Compound of Example 5 | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

| Formulation 6 | |
|---|---|
| Suppositories, each containing 225 mg of active ingredient, are made as follows: | |
| Compound of Example 6 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

| Formulation 7 | |
|---|---|
| Suspensions, each containing 50 mg of active ingredient per 5 ml dose, are made as follows: | |
| Compound of Example 7 | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

| Formulation 8 | |
|---|---|
| An intravenous formulation may be prepared as follows: | |
| Compound of Example 1 | 100 mg |
| Isotonic saline | 1,000 ml |

The solution of the above ingredients generally is administered intravenously to a subject at a rate of 1 ml per minute.

ASSAY EXPERIMENTS

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992 (the disclosure of which is incorporated herein by reference):

Reagents:
REACTION BUFFER—
$CaCl_2 \cdot 2H_2O$ (1.47 g/L)
KCl (7.455 g/L)
Bovine Serum Albumin (fatty acid free) (1 g/L)(Sigma A-7030, product of Sigma Chemical Co., St. Louis Mo., USA)
TRIS HCl (3.94 g/L)
TRIS=(tris(hydroxymethyl)aminomethane) pH 7.5 (adjust with NaOH)
ENZYME BUFFER—
0.05 $NaOAc \cdot 3H_2O$, pH 4.5
0.2 NaCl
Adjust pH to 4.5 with acetic acid
DTNB—
5,5'-dithiobis-2-nitrobenzoic acid
RACEMIC DIHEPTANOYL THIO—PC
racemic 1,2-bis(heptanoylthio)-1,2-dideoxy-sn-glycero-3-phosphorylcholine
TRITON X-100 prepare at 6.249 mg/ml in reaction buffer to equal 10 uM
TRITON X-100 is a polyoxy ethylene non-ionic detergent supplied by Pierce Chemical Company, 3747 N. Meridian Road, Rockford, Ill. 61101.
REACTION MIXTURE—
A measured volume of racemic dipheptanoyl thio PC supplied in chloroform at a concentration of 100 mg/ml is taken to dryness and redissolved in 10 millimolar TRITON X-100 nonionic detergent aqueous solution. Reaction Buffer is added to the solution, then DTNB to give the Reaction Mixture.

The reaction mixture thus obtained contains 1 mM diheptanoly thio-PC substrate, 0.29 mm TRITON X-100 detergent, and 0.12 mm DTMB in a buffered aqueous solution at pH 7.5.

Assay Procedure
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the $IC_{50}$ values were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ were determined by plotting log concentration versus inhibition values in the range from 10–90% inhibition.

Compounds of the instant invention were tested in Assay Example 1 and afforded the following results.

| Results | |
|---|---|
| Compound of Example# | $IC_{50}$ (nM) (nanomolar) |
| 1 | 18.3 |
| 2 | 18.7 |
| 3 | 19.3 |
| 4 | 17.0 |
| 5 | 42.5 |
|   | 12.0 |
| 7 | 29.0 |

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 mL jacketed tissue baths maintained at 37° C. The tissue baths were continuously aerated and contained a modified Krebs solution of the following composition (millimolar) NaCl, 118.2; KCl, 4.6; $CaCl_2 \cdot 2H_2O$, 2.5; $MgSO_4 \cdot 7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative Concentration-response Curves

Initially tissues were challenged 3 times with KCl (40 mM) to test tissue viability and to obtain a consistent response. After recording the maximal response to KCl, the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.). Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of sPLA$_2$, the compounds and their respective vehicles were added to the tissues 30 minutes prior to starting the sPLA$_2$ concentration-response curves.
Statistical Analysis Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the ED$_{50}$ for the control curve, the steepness of the curves, and the pA$_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent K$_B$, the dissociation constant of the inhibitor.

To estimate the drug-induced suppression of the maximal responses, sPLA$_2$ responses (10 ug/ml) were determined in the absence and presence of drug, and percent suppression was calculated for each pair of tissues Ref. 1—Van, J. M.: Cumulative dose-response curves. II. Technique for the making of dose-response curves in isolated organs and the evaluation of drug parameters. *Arch. Int. Pharmacodyn. Ther.*, 143: 299–330, 1963.

Ref. 2—Waud, D.: Analysis of dose-response relationships. in *Advances in General and Cellular Pharmacology* eds Narahashi, Bianchi 1:145–178, 1976.

Compounds of the instant invention were tested in Assay Example 2 and were found to be effective at concentrations below 20 μM.

Assay Example 3 sPLA$_2$ Transgenic Mice Assay

Materials & Methods

The mice utilized in these studies were mature, 6–8 month old, ZnSO$_4$-stimulated, hemizygous line 2608$^a$ transgenic mice (Fox et. al. 1996). Transgenic mice from this line express human sPLA$_2$ in the liver and other tissues and typically achieve levels of human sPLA$_2$ in their circulation of approximately 173±10 ng/ml when maximally stimulated with ZnSO$_4$ (Fox, et al. 1996). The mice were housed under constant humidity and temperature and received food and water ad libitum. Animal room lighting was maintained on a 12-hour light/dark cycle and all experiments were performed at the same time of the day during the early morning light period.

For intravenous testing, compounds or vehicle were administered as an IV bolus via the tail vein in a volume of 0.15 ml. Vehicle consisted of 1–5% dimethylsulfoxide, 1–5% ethanol and 10–30% polyethylene glycol 300 in H$_2$O; the concentrations of these ingredients were adjusted according to the solubility of the compound. Mice were bled retro-orbitally prior to drug or vehicle administration and 30 minutes, 2 and 4 hours thereafter. Three to six mice were used for each dose. PLA$_2$ catalytic activity in the serum was assayed with a modified phosphatidylcholine/deoxycholine mixed micelle assay (Fox, et al. 1996, Schadlich, et al., 1987) utilizing 3 mM sodium deoxycholate and 1 mM 1-palmitoyl-2-oleoyl-sn-glycero-3-phosphocholine.

For oral testing, compounds were dissolved in 1–5% ethanol/10–30% polyethylene glycol 300 in H$_2$O or were suspended in 5% dextrose in H$_2$O and administered by oral gavage. Serum was prepared from retro-orbital blood and assayed for PLA$_2$ catalytic activity as above.

REFERENCES

Fox, N., M. Song, J. Schrementi, J. D. Sharp, D. L. White, D. W. Snyder, L. W. Hartley, D. G. Carlson, N. J. Bach, R. D. Dillard, S. E. Draheim, J. L. Bobbitt, L. Fisher and E. D. Mihelich. 1996. Eur. J. Pharmacol. 308: 195. Schadlich, H. R., M. Buchler, and H. G. Beger, 1987, *J. Clin. Chem. Clin. Biochem.* 25, 505.

Compounds of the instant invention were tested in Assay Example 3 and were found to be effective.

While the present invention has been illustrated above by certain specific embodiments, it is not intended that these specific examples should limit the scope of the invention as described in the appended claims.

We claim:

1. A compound of the formula (I):

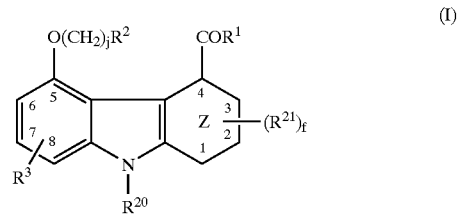

(I)

Z is cyclohexenyl, or phenyl,

R$^{20}$ is selected from groups (a), (b) and (c) where;
  (a) is —(C$_1$-C$_{20}$)alkyl, —(C$_2$-C$_{20}$)alkenyl, —(C$_2$-C$_{20}$)alkynyl, carbocyclic radicals, or heterocyclic radicals, or
  (b) is a member of (a) substituted with one or more substituents selected from hydrogen, —(C$_1$-C$_6$) alkyl, —(C$_2$-C$_6$)alkenyl, —(C$_2$-C$_6$)alkynyl, —(C$_3$-C$_8$)cycloalkyl," —(C$_1$-C$_8$)alkoxy, halogen or phenyl (C$_1$-C$_4$)alkyl,
  (c) is the group —(L)—R$^{80}$; where, (L)— is a divalent linking group of 1 to 12 atoms selected from carbon, hydrogen, R$^{21}$ is hydrogen, —(C$_1$-C$_6$)alkyl, —(C$_2$-C$_6$)alkenyl, —(C$_2$-C$_6$)alkynyl, —(C$_3$-C$_8$)cycloalkyl," —(C$_1$-C$_6$) alkoxy, halogen or phenyl (C$_1$-C$_4$)alkyl, where f is 1–3;

R$^1$ is —NHNR$^{30}$R$^{31}$, —NR$^{30}$R$^{31}$, or —CONR$^{30}$R$^{31}$, where R$^{30}$ and R$^{31}$ are each independently hydrogen or —(C$_1$-C$_6$)alkyl;

R$^2$ is —CONR$^{40}$R$^{41}$, where R$^{40}$ —OH, —O(C$_1$-C$_8$)alkyl, —O(C$_2$-C$_8$)alkenyl, —O(C$_3$-C$_8$)cycloalkyl, —O(aryl) and —O(C$_1$-C$_8$)alkylaryl; and R$^{41}$ is hydrogen, —(C$_1$-C$_8$)alkyl, —(C$_2$-C$_8$)alkenyl, —(C$_3$-C$_8$) cycloalkyl, aryl and —(C$_1$-C$_8$)alkylaryl;

where j is 1 to 3 both inclusive; and

R$^3$ is selected from hydrogen, —(C$_1$-C$_6$)alkyl, —(C$_2$-C$_6$) alkenyl, —(C$_2$-C$_6$)alkynyl, —(C$_3$-C$_8$)cycloalkyl," —(C$_1$-C$_6$)alkoxy, halogen, phenyl (C$_1$-C$_4$)alkyl, optionally substituted carbocyclic and optionally substituted heterocyclic, wherein the substituent is selected from hydrogen, —(C$_1$-C$_6$)alkyl, —(C$_2$-C$_6$)alkenyl, —(C$_2$-C$_6$)alkynyl, —(C$_3$-C$_8$)cycloalkyl," —(C$_1$-C$_6$) alkoxy, halogen and phenyl (C$_1$-C$_4$)alkyl, or a pharmaceutically acceptable solvate or salt, thereof.

2. A compound of the formula (III):

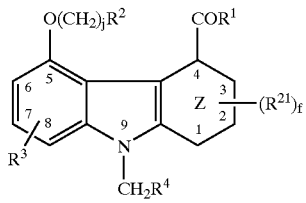

(III)

wherein;
Z is cyclohexenyl, or phenyl,
R$^1$ is —NHNR$^{30}$R$^{31}$, —NR$^{30}$R$^{31}$, or —CONR$^{30}$R$^{31}$, where R$^{30}$ and R$^{31}$ are each independently hydrogen or —(C$_1$-C$_6$)alkyl;)
R$^2$ is —CONR$^{40}$R$^{41}$, where R$^{40}$ is —OH, —O(C$_1$-C$_8$)alkyl, —O(C$_2$-C$_8$)alkenyl, —O(C$_3$-C$_8$)cycloalkyl, —O(aryl) or —O(C$_1$-C$_8$)alkylaryl; and R$^{41}$ is hydrogen, —(C$_1$-C$_8$)alkyl, —(C$_2$-C$_8$)alkenyl, —(C$_3$-C$_8$)cycloalkyl, aryl or —(C$_1$-C$_8$)alkylaryl;
where j is 1 to 3 both inclusive;
R$^3$ is hydrogen, —O(C$_1$-C$_6$)alkyl, halo, —(C$_1$-C$_6$)alkyl, —(C$_2$-C$_6$)alkenyl, —(C$_2$-C$_6$)alkynyl, —(C$_3$-C$_8$) cycloalkyl, phenyl, —(C$_1$-C$_4$)alkylphenyl; phenyl substituted with —(C$_1$-C$_6$)alkyl, halo, or —CF$_3$; —CH$_2$OSi(C$_1$-C$_6$)$_3$alkyl, furyl, thiophenyl, —(C$_1$-C$_6$) hydroxyalkyl, —(C$_1$-C$_6$)alkoxy(C$_1$-C$_6$)alkyl, —(C$_1$-C$_6$)alkoxy(C$_1$-C$_6$)alkenyl, and —(CH$_2$)$_n$R$^8$, where R$^8$ is hydrogen, —CONH$_2$, —NR$^9$R$^{10}$, —CN or phenyl, where R$^9$ and R$^{10}$ are independently hydrogen, —CF$_3$, phenyl, —(C$_1$-C$_4$)alkyl, —(C$_1$-C$_4$)alkylphenyl or -phenyl(C$_1$-C$_4$)alkyl and n is 1 to 8; and
R$^4$ is hydrogen, —(C$_1$-C$_{14}$)alkyl, —(C$_3$-C$_{14}$)cycloalkyl, pyridyl, phenyl or phenyl substituted with from 1–5 substituents selected from the group consisting of —(C$_1$-C$_6$)alkyl, halo, —CF$_3$, —OCF$_3$, —(C$_1$-C$_4$) alkoxy, —CN, —(C$_1$-C$_4$)alkylthio, —(C$_1$-C$_4$) alkylphenyl, phenyl, phenoxy and —OR$^9$; where R$^9$ is independently hydrogen, —CF$_3$, phenyl, —(C$_1$-C$_4$) alkyl, —(C$_1$-C$_4$)alkylphenyl; tetrazole or tetrazole substituted with —(C$_1$-C$_4$)alkyl or —(C$_1$-C$_4$)alkylphenyl; or naphthyl; and
R$^{21}$ is hydrogen, halo, —(C$_1$-C$_3$)alkyl, —(C$_3$-C$_4$) cycloalkyl, —(C$_3$-C$_8$)cycloalkenyl, —O(C$_1$-C$_2$)alkyl and —S(C$_1$-C$_2$)alkyl where f is 1 to 3 or a pharmaceutically acceptable solvate or salt, thereof.

3. A compound of formula III as claimed in claim 2 wherein:
R$^1$ is —NH$_2$
R$^2$ is —CONR$^{40}$R$^{41}$ where R$^{40}$ is —OH, —O(C$_1$-C$_8$) alkyl, —O(C$_2$-C$_8$)alkenyl, —O(C$_3$-C$_8$)cycloalkyl, —O(aryl) or —O(C$_1$-C$_8$)alkylaryl; and R$^{41}$ hydrogen, —(C$_1$-C$_8$)alkyl, —(C$_2$-C$_8$)alkenyl, —(C$_3$-C$_8$) cycloalkyl, aryl or —(C$_1$-C$_8$)alkylaryl;
where j is 1;
R$^3$ is hydrogen, —(C$_1$-C$_6$)alkyl, —(C$_2$-C$_6$)alkenyl, —(C$_2$-C$_6$)alkynyl, —(C$_3$-C$_8$)cycloalkyl, —(C$_1$-C$_6$) alkoxy, halo or -phenyl (C$_1$-C$_4$)alkyl;
R$^4$ is phenyl or phenyl substituted with from 1–5 substituents selected from the group consisting of —(C$_1$-C$_6$)alkyl, halo, —CF$_3$, —OCF$_3$, —(C$_1$-C$_4$) alkoxy, —CN, —(C$_1$-C$_4$)alkylthio, phenyl (C1-C$_4$) alkyl, —(C$_1$-C$_4$)alkylphenyl, phenyl, phenoxy or —OR$^9$; where R$^9$ is independently hydrogen, —CF$_3$, phenyl, —(C$_1$-C$_4$)alkyl, —(C$_1$-C$_4$)alkylphenyl or -phenyl(C$_1$-C$_4$)alkyl; tetrazole; tetrazole substituted with —(C$_1$-C$_4$)alkyl or —(C$_1$-C$_4$)alkylphenyl;
R$^{21}$ is hydrogen, halo, —(C$_1$-C$_3$)alkyl, —(C$_3$-C$_4$) cycloalkyl, —(C$_3$-C$_4$)cycloalkenyl, —O(C$_1$-C$_2$)alkyl and —S(C$_1$-C$_2$)alkyl where f is 1; and
Z is phenyl or a pharmaceutically acceptable solvate or salt thereof.

4. A compound of formula III as claimed in claim 2 wherein:
R$^{21}$ is hydrogen;
R$^3$ is hydrogen; and
R$^4$ is phenyl or phenyl substituted with from 1–5 substituents selected from the group consisting of —(C$_1$-C$_6$)alkyl, halo, —CF$_3$, —OCF$_3$, —(C$_1$-C$_4$) alkoxy, —CN, —(C$_1$-C$_4$)alkyithio, phenyl (C$_1$-C$_4$) alkyl, —(C$_1$-C$_4$)alkylphenyl, phenyl, phenoxy or —OR$_9$; where R$^9$ is independently hydrogen, —CF$_3$, phenyl, —(C$_1$-C$_4$)alkyl, —(C$_1$-C$_4$)alkylphenyl or -phenyl (C$_1$-C$_4$)alkyl;
or a pharmaceutically acceptable solvate or salt thereof.

5. A compound selected from the group consisting of;
[[5-Carbamoyl-9-(phenylmethyl)carbazol-4-yl]oxy]-N-(hydroxy)acetamide;
[[5-Carbamoyl-9-(phenylmethyl)carbazol-4-yl]oxy]-N-(methoxy)acetamide
[[5-Carbamoyl-9-(phenylmethyl)carbazol-4-yl]oxy]-N-(ethoxy)acetamide;
[[5-Carbamoyl-9-(phenylmethyl)carbazol-4-yl]oxy]-N-[(phenylmethyl)oxy]acetamide;
[[5-Carbamoyl-9-(phenylmethyl)carbazol-4-yl]oxy]-N-(methoxy)-N-(methyl)acetamide;
[[5-Carbamoyl-9-(phenylmethyl)carbazol-4-yl]oxy]-N-(phenyloxy)acetamide;
[[5-Carbamoyl-9-(phenylmethyl)-2-(thien-2-yl)carbazol-4-yl]oxy]-N-[(phenylmethyl) oxy]acetamide;
or a pharmaceutically acceptable solvate or salt thereof.

6. A pharmaceutical formulation comprising a compound of formula I as claimed in claim 1 together with a pharmaceutically acceptable carrier or diluent therefor.

7. A method of selectively inhibiting sPLA$_2$ in a mammal in need of such treatment comprising administering to said mammal a therapeutically effective amount of a compound according to claim 1.

8. A method of selectively inhibiting sPLA$_2$ in a mammal in need of such treatment comprising administering to said mammal a therapeutically effective amount of a compound according to claim 2.

9. A method of claim 8 wherein the mammal is a human.

10. A method of inhibiting sPLA$_2$ which comprises contacting the sPLA$_2$ with a compound of formula I as claimed in claim 1.

11. A method of treating a condition selected from the group consisting of sepsis, septic shock, adult respiratory distress syndrome, pancreatitis, trauma-induced shock, asthma, rheumatoid arthritis, osteoarthritis, acute bronchitis, chronic bronchitis and Inflammatory Bowel Disease which comprises administering to a subject in need of such treatment, a therapeutically effective amount of a compound of claim 1.

12. A method of treating a condition selected from the group consisting of sepsis, septic shock, adult respiratory distress syndrome, pancreatitis, trauma-induced shock, asthma, rheumatoid arthritis, osteoarthritis, acute bronchitis, chronic bronchitis and Inflammatory Bowel Disease which comprises administering to a subject in need of such treatment, a therapeutically effective amount of a compound according to claim 2.

* * * * *